(12) United States Patent
Balestrieri

(10) Patent No.: US 11,273,176 B2
(45) Date of Patent: Mar. 15, 2022

(54) USE OF PLA2G5-DEFICIENT SUPPRESSIVE MACROPHAGES IN SUPPRESSION OF INFLAMMATION

(71) Applicant: THE BRIGHAM AND WOMEN'S HOSPITAL, INC., Boston, MA (US)

(72) Inventor: Barbara Balestrieri, Marblehead, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 551 days.

(21) Appl. No.: 16/080,905

(22) PCT Filed: Mar. 2, 2017

(86) PCT No.: PCT/US2017/020479
§ 371 (c)(1),
(2) Date: Aug. 29, 2018

(87) PCT Pub. No.: WO2017/151939
PCT Pub. Date: Sep. 8, 2017

(65) Prior Publication Data
US 2019/0105347 A1 Apr. 11, 2019

Related U.S. Application Data

(60) Provisional application No. 62/393,244, filed on Sep. 12, 2016, provisional application No. 62/314,136, filed on Mar. 28, 2016, provisional application No. 62/302,251, filed on Mar. 2, 2016.

(51) Int. Cl.
| | | |
|---|---|---|
| A61K 35/15 | (2015.01) | |
| C12N 15/113 | (2010.01) | |
| A61P 11/06 | (2006.01) | |
| A61P 29/00 | (2006.01) | |
| A61K 38/19 | (2006.01) | |
| C12N 5/0786 | (2010.01) | |

(52) U.S. Cl.
CPC ............ *A61K 35/15* (2013.01); *A61K 38/19* (2013.01); *A61P 11/06* (2018.01); *A61P 29/00* (2018.01); *C12N 5/0645* (2013.01); *C12N 15/113* (2013.01); *C12N 2310/14* (2013.01); *C12N 2501/22* (2013.01)

(58) Field of Classification Search
None
See application file for complete search history.

(56) References Cited

U.S. PATENT DOCUMENTS

| 7,416,853 | B2 | 8/2008 | MacPhee et al. |
| 8,609,357 | B2 | 12/2013 | Shou et al. |
| 2005/0164238 | A1 | 7/2005 | Valkirs et al. |
| 2005/0209440 | A1 | 9/2005 | Canne et al. |
| 2011/0142812 | A1 | 6/2011 | Du Clos et al. |
| 2013/0236437 | A1 | 9/2013 | Bishopric et al. |
| 2015/0174204 | A1 | 6/2015 | Heslet |

FOREIGN PATENT DOCUMENTS

WO WO 2016/011930 1/2016

OTHER PUBLICATIONS

Hagedorn et al. Nucleic Acids Research 45, 2262-2282 (Year: 2017).*
Fakhr et al. Cancer Gene Therapy 23, 73-82 (Year: 2016).*
Alvarez-Curto and Milligan, "Metabolism meets immunity: The role of free fatty acid receptors in the immune system," Biochemical Pharmacology, 2016, 114: 3-13.
Balestrieri et al., "Group V secretory phospholipase A2 translocates to the phagosome after zymosan stimulation of mouse peritoneal macrophages and regulates phagocytosis," The Journal of Biological Chemistry, 2006, 281(10): 6691-6698.
Barlow et al., "Innate IL-13-producing nuocytes arise during allergic lung inflammation and contribute to airways hyperreactivity," The Journal of Allergy and Clinical Immunology, 2012, 129(1): 191-198 e191-194.
Barlow et al., "IL-33 is more potent than IL-25 in provoking IL-13-producing nuocytes (type 2 innate lymphoid cells) and airway contraction," The Journal of Allergy and Clinical Immunology, 2013, 132(4): 933-941.
Bartemes et al., "IL-33-responsive lineage—CD25+ CD44(hi) lymphoid cells mediate innate type 2 immunity and allergic inflammation in the lungs," Journal of Immunology, 2012, 188(3): 1503-1513.
Bøyum et al., "Isolation of mononuclear cells and granulocytes from human blood. Isolation of monuclear cells by one centrifugation, and of granulocytes by combining centrifugation and sedimentation at 1 g," Scand J Clin Lab Invest Suppl, 1968, 97: 77-89.
Briscoe et al., "The orphan G protein-coupled receptor GPR40 is activated by medium and long chain fatty acids," The Journal of Biological Chemistiy, 2003, 278(13): 11303-11311.
Chang et al., "Innate lymphoid cells mediate influenza-induced airway hyper-reactivity independently of adaptive immunity," Nature Immunology, 2011, 12(7): 631-638.
Christiansen et al., "Activity of dietary fatty acids on FFA1 and FFA4 and characterization of pinolenic acid as a dual FFA1/FFA4 agonist with potential effect against metabolic diseases," The British Journal of Nutrition, 2015, 113(11): 1677-1688.
Conese et al., "Hematopoietic and Mesenchymal Stem Cells for the Treatment of Chronic Respiratory Diseases: Role of Plasticity and Heterogeneity," The Scientific World Journal, 2014, 2014:859817.
de Almeida et al., "A Simple Method for Human Peripheral Blood Monocyte Isolation," Mem Inst Oswaldo Cruz, Mar./Apr. 2000, 95: 221-223.

(Continued)

*Primary Examiner* — Brian Whiteman
(74) *Attorney, Agent, or Firm* — Fish & Richardson P.C.

(57) ABSTRACT

Methods to reduce the inflammatory response critical in the pathogenesis of asthma and asthma exacerbations via the introduction of autologous Pla2g5-deficient suppressive macrophages into the airways of patients with asthma.

20 Claims, 16 Drawing Sheets
Specification includes a Sequence Listing.

(56) References Cited

OTHER PUBLICATIONS

Dennis et al., "Phospholipase A2 enzymes: physical structure, biological function, disease implication, chemical inhibition, and therapeutic intervention," Chemical Reviews, 2011, 111(10): 6130-6185.
Doherty et al., "STAT6 regulates natural helper cell proliferation during lung inflammation initiated by Alternaria," American Journal of Physiology, 2012, 303(7): L577-588.
Doherty et al., "Lung type 2 innate lymphoid cells express cysteinyl leukotriene receptor 1, which regulates TH2 cytokine production," The Journal of Allergy and Clinical Immunology, 2013, 132(1): 205-213.
Doherty et al., "Alternaria induces STAT6-dependent acute airway eosinophilia and epithelial FIZZ1 expression that promotes airway fibrosis and epithelial thickness," Journal of Immunology, 2012, 188(6): 2622-2629.
Elkord et al., "Human monocyte isolation methods influence cytokine production from in vitro generated dendritic cells," Immunology, 2005, 114: 204-212.
Giannattasio et al., "Group V secretory phospholipase A2 reveals its role in house dust mite-induced allergic pulmonary inflammation by regulation of dendritic cell function," Journal of Immunology, 2010, 185(7): 4430-4438.
Gorski et al., "Group 2 innate lymphoid cell production of IL-5 is regulated by NKT cells during influenza vims infection," PloS Pathogens, 2013, 9(9): e1003615.
Halim et al., "Lung natural helper cells are a critical source of Th2 cell-type cytokines in protease allergen-induced airway inflammation," Immunity, 2012, 36(3): 451-463.
Halim et al., "Retinoic-acid-receptor-related orphan nuclear receptor alpha is required for natural helper cell development and allergic inflammation," Immunity, 2012, 37(3): 463-474.
Halim et al., "Group 2 innate lymphoid cells are critical for the initiation of adaptive T helper 2 cell-mediated allergic lung inflammation," Immunity, 2014, 40(3): 425-435.
Hardman et al., "IL-33 citrine reporter mice reveal the temporal and spatial expression of IL-33 during allergic lung inflammation," European Journal of Immunology, 2013, 43(2): 488-498.
Heng and Painte, "The Immunological Genome Project: networks of gene expression in immune cells," Nature Immunology, 2008, 9(10): 1091-1094.
Hirasawa et al., "Free fatty acids regulate gut incretin glucagon-like peptide-1 secretion through GPR120," Nature Medicine, 2005, 11(1): 90-94.
International Preliminary Report on Patentability in International Application No. PCT/US2017/020479, dated Sep. 4, 2018.
International Search Report and Written Opinion in International Application No. PCT/US2017/020479, dated Jun. 6, 2017, 14 pages.
Ishitaniti et al., "Influence of arachidonate metabolism on enhancement of intracellular transglutaminase activity in mouse peritoneal macrophages," J Biochem, 1988, 104: 397-402.
Itoh et al., "Free fatty acids regulate insulin secretion from pancreatic beta cells through GPR40," Nature, 2003, 422(6928): 173-176.
Kean et al., "MSCs: Delivery Routes and Engraftment, Cell-Targeting Strategies, and Immune Modulation," Stem Cells International, 2013, 2013: 732742.
Kim et al., "Innate lymphoid cells responding to IL-33 mediate airway hyperreactivity independently of adaptive immunity," The Journal of Allergy and Clinical Immunology, 2012, 129(1): 216-227 e211-216.
Kotarsky et al., "A human cell surface receptor activated by free fatty acids and thiazolidinedione drugs," Biochemical and Biophysical Research Communications, 2003, 301(2): 406-410.
Kouzaki et al., "The danger signal, extracellular ATP, is a sensor for an airborne allergen and triggers IL-33 release and innate Th2-type responses," Journal of Immunology, 2011, 186(7): 4375-4387.

Lee et al., "Activated type 2 innate lymphoid cells regulate beige fat biogenesis," Cell, 2015, 160(1-2): 74-87.
Licona-Limon et al., "TH2, allergy and group 2 innate lymphoid cells," Nature Immunology, 2013, 14(6): 536-542.
Makrinioti et al., "Role of interleukin 33 in respiratory allergy and asthma," The Lancet Respiratory Medicine, 2014, 2(3): 226-237.
Mia et al., "An optimized Protocol for Human M2 Macrophages using M-CSF and IL-4/IL-10/TGF-$\beta$ Yields a Dominant Immunosuppressive Phenotype," Scand J Immunol, 2014, 79(5):305-14.
Molofsky et al., "Innate lymphoid type 2 cells sustain visceral adipose tissue eosinophils and alternatively activated macrophages," The Journal of Experimental Medicine, 2013, 210(3): 535-549.
Moro et al., "Innate production of T(H)2 cytokines by adipose tissue-associated c-Kit(+)Sca-1(+) lymphoid cells," Nature, 2010, 463(7280): 540-544.
Munoz et al., "Deletion of secretory group V phospholipase A2 attenuates cell migration and airway hyperresponsiveness in immunosensitized mice," Journal of Immunology, 2007, 179(7): 4800-4807.
Murakami et al., "Distinct arachidonate-releasing functions of mammalian secreted phospholipase A2s in human embryonic kidney 293 and rat mastocytoma RBL-2H3 cells through haract sulfate shuttling and external plasma membrane mechanisms," The Journal of Biological Chemistry, 2001, 276(13): 10083-10096.
Murakami et al., "Emerging roles of secreted phospholipase A2 enzymes: The 3rd edition," Biochimie, 2014; 107 Pt A: 105-113.
Murdoch and Lloyd, "Chronic inflammation and asthma," Mutat Res, 2010, 690(1-2): 24-39.
Neill et al., "Nuocytes represent a new innate effector leukocyte that mediates type-2 immunity," Nature, 2010, 464(7293): 1367-1370.
Oh et al., "Pessentheiner AR et al. A Gpr120-selective agonist improves insulin resistance and chronic inflammation in obese mice," Nature Medicine, 2014, 20(8): 942-947.
Ohradanova-Repic et al., "Differentiation of human monocytes and derived subsets of macrophages and dendritic cells by the HLDA10 monoclonal antibody panel," Clinical & Translational Immunology (2016) 5, e55.
Ohta et al., "Group V secretory phospholipase A2 is involved in macrophage activation and is sufficient for macrophage effector functions in allergic pulmonary inflammation," Journal of Immunology, 2013, 190(12): 5927-5938.
Ohtsuki et al., "Transgenic Expression of Group V, but Not Group X, Secreted Phospholipase A2 in Mice Leads to Neonatal Lethality because of Lung Dysfunction," Journal of Biological Chemistry, 281: 36420-36433.
Polumuri et al., Transcriptional regulation of murine IL-33 by TLR and non-TLR agonists, Journal of Immunology, 2012; 189(1): 50-60.
Price et al., "Systemically dispersed innate IL-13-expressing cells in type 2 immunity," PNAS, 2010; 107(25): 11489-11494.
Quehenberger et al., Lipidomics reveals a remarkable diversity of lipids in human plasma, Journal of Lipid Research, 2010, 51(11): 3299-3305.
Quehenberger et al., "High sensitivity quantitative lipidomics analysis of fatty acids in biological samples by gas chromatography-mass spectrometry," Biochimica et Biophysica Acta, 2011, 1811(11): 648-656.
Rubio et al., "Group V secreted phospholipase A2 is upregulated by IL-4 in human macrophages and mediates phagocytosis via hydrolysis of ethanolamine phospholipids," J Immunol, Apr. 2015, 194: 3327-39.
Satake et al., "Role of Group V Phospholipase A2 in Zymosan-induced Eicosanoid Generation and Vascular Permeability Revealed by Targeted Gene Disruption," The Journal of Biological Chemistry, Apr. 2004, 279: 16488-16494.
Sato et al., "The adipocyte-inducible secreted phospholipases PLA2G5 and PLA2G2E play distinct roles in obesity," Cell Metabolism, 2014, 20(1): 119-132.
Singer et al., "Interfacial kinetic and binding properties of the complete set of human and mouse groups I, II, V, X, and XII secreted phospholipases A2," The Journal of Biological Chemistry 2002, 277(50): 48535-48549.

(56) References Cited

OTHER PUBLICATIONS

Stevens et al., "Detection and quantitation of eosinophils in the murine respiratory tract by flow cytometry," Journal of Immunological Methods, 2007; 327(1-2): 63-74.

Tomoo et al., "Design, synthesis, and biological evaluation of 3-(1-Aryl-1H-indol-5-yl)propanoic acids as new indole-based cytosolic phospholipase A2α inhibitors," Sep. 2014, 57: 7244-62.

Van Dyken et al., "Chitin activates parallel immune modules that direct distinct inflammatory responses via innate lymphoid type 2 and gammadelta T cells," Immunity, 2014, 40(3): 414-424.

Wills-Karp et al., "Trefoil factor 2 rapidly induces interleukin 33 to promote type 2 immunity during allergic asthma and hookworm infection," The Journal of Experimental Medicine, 2012, 209(3): 607-622.

Wojno et al., "The prostaglandin D(2) receptor CRTH2 regulates accumulation of group 2 innate lymphoid cells in the inflamed lung," Mucosal Immunology, 2015, 8(6): 1313-1323.

Yamaguchi et al., "PLA2G5 Regulates Transglutaminase Activity of Human IL-4-Activated M2 Macrophages Through PGE2 Generation," Journal of Leukocyte Biology, 2016, 100: 131-141.

Menck et al., "Isolation of Human Monocytes by Double Gradient Centrifugation and Their Differentiation to Macrophages in Teflon-coated Cell Culture Bags," J. Vis. Exp, 2014, (91): e51554.

Yu et al., "Innate lymphoid cells and asthma," The Journal of Allergy and Clinical Immunology, 2014, 133(4): 943-950.

Yamaguchi et al., "Macrophages regulate lung ILC2 activation via Pla2g5-dependent mechanisms," May 2018, 11:615-626.

Pulimood et al., "Epidemic asthma and the role of the fungal mold Alternaria alternate," Journal of Allergy and Clinical Immunology, Sep. 1, 2007, 120(3):610-7.

Salo et al., "Dustborne Alternaria alternata antigens in US homes: results from the National Survey of Lead and Allergens in Housing," Journal of Allergy and Clinical Immunology, Sep. 1, 2005, 116(3):623-9.

\* cited by examiner

CD45+CD68+IL-33+

USE OF PLA2G5-DEFICIENT SUPPRESSIVE MACROPHAGES IN SUPPRESSION OF INFLAMMATION

CLAIM OF PRIORITY

This application is a § 371 National Stage Application of PCT/US2017/020479, filed Mar. 2, 2017, which claims the benefit of U.S. Provisional Application Ser. No. 62/302,251, filed on Mar. 2, 2016; 62/314,136, filed on Mar. 28, 2016; and 62/393,244, filed on Sep. 12, 2016. The entire contents of the foregoing are incorporated herein by reference.

FEDERALLY SPONSORED RESEARCH OR DEVELOPMENT

This invention was made with Government support under Grant No. R01HL113071 awarded by the National Institutes of Health. The Government has certain rights in the invention.

TECHNICAL FIELD

Described herein are methods to reduce the inflammatory response critical in the pathogenesis of asthma and asthma exacerbations via the introduction of autologous Pla2g5-deficient suppressive macrophages into the airways of patients with asthma.

BACKGROUND

Asthma is a heterogeneous chronic disease characterized by persistent pulmonary inflammation, episodic bronchoconstriction, and airway remodeling. *Alternaria Alternata* is a common fungus that is a source of allergens associated with the development of asthma and asthma exacerbations. In mice, *Alternaria* allergens trigger accumulation of eosinophils and the development of airway hyperreactivity[1, 2], each of which prominently involves effectors of the innate immune system[1, 3, 4]. Acute exposure of the airways of naïve mice to *Alternaria* causes the rapid release of IL-33 by epithelial cells, followed by the activation of group 2 innate lymphoid cells (ILC2)[3, 5]. Longer term repetitive administration of *Alternaria* upregulates lung expression of IL-33, and promotes incremental ILC2-dependent lung eosinophilic inflammation[1]. ILC2s lack cell surface markers associated with major hematopoietic lineages (Lin)[6-8]. In the lung they express Thy1.2 (CD45+ Lin− Thy1.2+)[9] and activation molecules including ST2 (IL1R1), Sca-1, CD278 (ICOS), CD25 (IL-2Rα), CD127 (IL-7Rα), CD117 (c-Kit), and IL-17RB (IL-25R)[1, 10-12]. Following activation, ILC2s produce IL-5 and IL-13 (as well as other cytokines), which mediate pulmonary eosinophilia, airway hyperreactivity[1, 12, 13] and macrophage activation[14]. Although IL-33 in naïve mouse lung is principally derived from structural cells[15], hematopoietic cell (including macrophages) can express IL-33 inducibly[16, 17]. Macrophages can activate ILC2 through an IL-33-dependent mechanism in a model of influenza-induced airway hyperreactivity[10].

SUMMARY

As described herein, the role of Pla2g5-expressing macrophages in activation of ILC2, IL-33 responsive cells, which were recently identified as key mediators in the pathogenesis of asthma and asthma exacerbations. In a mouse model of asthma induced by the fungus *Alternaria alternata* (characterized by increased numbers of eosinophils and ILC2 activation), mice lacking Pla2g5 had markedly reduced lung ILC2 activation and eosinophilia (FIG. 1). Furthermore, adoptive transfer of wild type (Wt) bone marrow-derived (BM)-macrophages (expressing Pla2g5) restored ILC2 activation and eosinophilia in *Alternaria*-exposed Pla2g5-null mice.

However, the transfer of Wt BM-macrophages into Pla2g5-null mice did not restore inflammation in Pla2g5-null mice to exactly the same levels of Wt mice (FIG. 4 of the manuscript). This data suggested that the inflammatory response of Pla2g5-null mice could be dampened by the presence of Pla2g5-null macrophages still present in the lung of Pla2g5-null mice receiving Wt BM-macrophages. To test this hypothesis, Pla2g5-null macrophages were transferred into Wt mice. Surprisingly, adoptive transfers of Pla2g5-null macrophages into the airways of Wt "asthmatic" mice induced a significant reduction of proinflammatory signatures of asthma (eosinophilia, and ILC2 activation, FIGS. 7A and 7B). These data indicate that Pla2g5-null macrophages have a "suppressive phenotype".

Thus, provided herein are methods for reducing pulmonary inflammation in a subject, e.g., a mammalian subject, preferably a human subject. The methods include delivering a population of cells comprising Pla2g5-deficient suppressive macrophages (preferably a population comprising at least 80% Pla2g5-deficient suppressive macrophages, e.g., at least 85%, 90%, 95%, or 99% pure Pla2g5-deficient suppressive macrophages) to a subject in need thereof, preferably to a lung or airway of the subject. In some embodiments, the methods include administering at least 0.5 million, 1 million, 2 million, or 4 million, or more, e.g., 0.25 to 5 million cells.

Also provided herein is a population of Pla2g5-deficient suppressive macrophages, at least 80% Pla2g5-deficient suppressive macrophages, e.g., at least 85%, 90%, 95%, or 99% pure Pla2g5-deficient suppressive macrophages, e.g., at least 0.5 million, 1 million, 2 million, or 4 million, or more, e.g., 0.25 to 5 million cells, for use in a method of reducing pulmonary inflammation in a subject, preferably wherein the macrophages are formulated for delivery to a lung or airway of a subject in need thereof.

In some embodiments, the population of Pla2g5-deficient suppressive macrophages is autologous to the subject.

In some embodiments, the population of Pla2g5-deficient suppressive macrophages comprises an inhibitory nucleic acid that specifically reduces expression of Pla2g5.

In some embodiments, the inhibitory nucleic acid is an antisense oligonucleotide, siRNA, shRNA, or CRISPR/Cas9 guide RNA.

In some embodiments, the inhibitory nucleic acid is modified, e.g., comprises a modified backbone or at least one modified nucleotide. In some embodiments, the inhibitory nucleic acid comprises at least one locked nucleic acid.

In some embodiments, the inhibitory nucleic acid is a gapmer or mixmer.

In some embodiments, the subject has asthma.

Also provided herein are methods for preparing a population of Pla2g5-deficient suppressive macrophages. The methods include obtaining a sample comprising peripheral blood from a subject (e.g., a subject who has pulmonary inflammation, e.g., asthma, and is in need of treatment using a method described herein); enriching the sample for mononuclear cells (CD14+ monocytes); and maintaining the mononuclear cells under conditions sufficient to promote differentiation of the mononuclear cells into a population of macrophages (CD64+ macrophages), e.g., culturing the cells for 7-14 days, e.g., 13 days, in culture medium containing the growth factor Granulocyte macrophage colony-stimulating factor (GMCSF) or MCSF; contacting the population of macrophages with an inhibitory nucleic acid that specifically reduces expression of Pla2g5, e.g., for about 24 hours; and activating the macrophages using IL-4 to express M2 markers (CCL22, TGM2), e.g., for about 6-48 hours, thereby preparing a population of Pla2g5-deficient suppressive macrophages (which have reduced expression of PLA2G5, and optionally also reduced expression of CCL22 and TGM2).

In some embodiments, the inhibitory nucleic acid is an antisense oligonucleotide, siRNA, shRNA, or CRISPR/Cas9 guide RNA.

In some embodiments, the inhibitory nucleic acid is modified, e.g., comprises a modified backbone or at least one modified nucleotide. In some embodiments, the inhibitory nucleic acid comprises at least one locked nucleic acid.

Also provided herein are populations of Pla2g5-deficient suppressive macrophages prepared by a method described herein, as well as methods of reducing pulmonary inflammation in a subject, comprising administering the population of Pla2g5-deficient suppressive macrophages to a subject in need thereof.

In some embodiments of the methods described herein, the cells are delivered by an aerosol spray of a suspension of cells into a nasal passage of the subject; by intratracheal or intrabracheal distillation; or by intravenous administration.

As used herein, the term "about" means plus or minus 10%.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
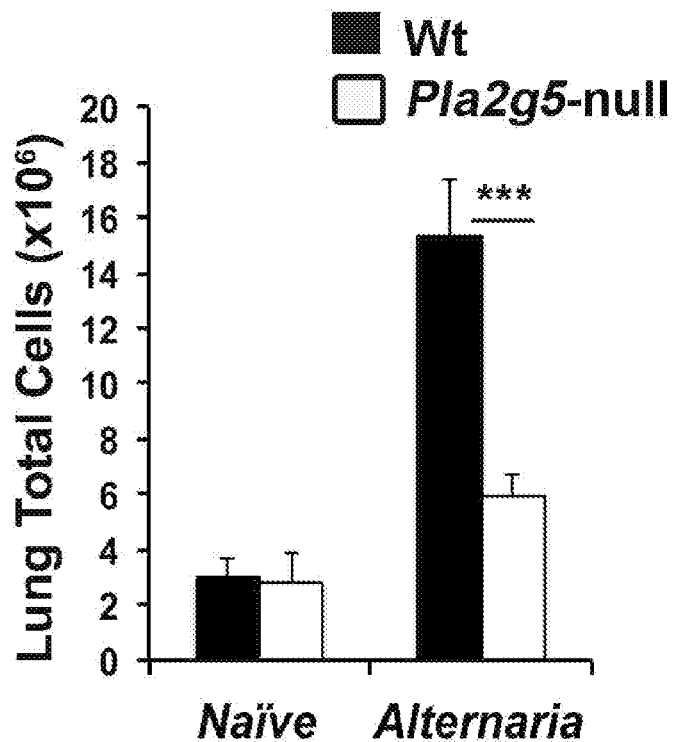
FIGS. 1A-E. *Alternaria*-induced pulmonary inflammation requires Pla2g5. (A) Total cell counts from homogenate lungs of naïve and *Alternaria*-treated Wt and Pla2g5-null mice. Analysis by flow cytometry of lung cell from naïve and *Alternaria*-treated Wt and Pla2g5-null homogenate lungs of eosinophils (B) gated as CD45+CD11c− SiglecF+; ILC2 (C) gated as CD45+ Lin− Thy1.2+; and (D) expression of Sca1, ST2, ICOS, CD25, and (E) intracellular IL-5 and IL-13 on ILC2. Values are mean±SEM of at least three independent experiments with 5-9 (naïve) or 10-21 (*Alternaria*-treated) mice per group. Images are from one representative mouse per group. * P<0.0005, P<0.005, *P<0.05.
Figure 1B:
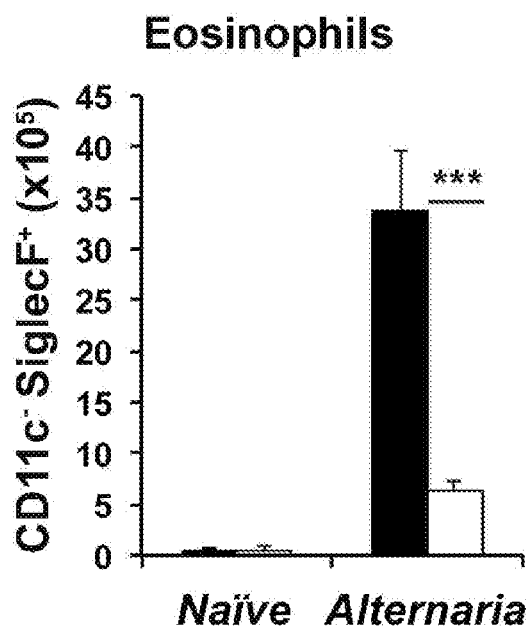

Phospholipases $A_2$ ($PLA_2$) are a family of enzymes that release lysophospholipids and free fatty acids (FFAs) from membrane glycerophospholipids[18, 19]. While FFAs such as arachidonic acid (AA) can be converted to receptor-active eicosanoids (including prostaglandins and leukotrienes), other FFAs can act directly at cognate receptors to regulate metabolic processes and inflammatory responses[20]. PLA2s may have substrate preferences and specific cell and tissue expression, therefore serving context-specific functions. Group V $PLA_2$ (Pla2g5) preferentially releases lysophosphatidylcholine (LPC) and the FFAs linoleic acid (LA) and oleic acid (OA)[21-23], and is prevalently expressed by innate immune cells, including dendritic cells and macrophages[24-26], as well as epithelial cells[25, 27]. Using a mouse model of allergic lung inflammation induced by the allergens of house dust mite *Dermatophagoides harac*, the present inventors demonstrated that Pla2g5 was necessary for the effector functions of both dendritic cells and macrophages[24, 25]. Adoptive transfer studies showed that Pla2g5 expression by macrophages was required for their generation of CCL22 and recruitment of T cells into the lungs[25].

As demonstrated herein, ILC2 activation is impaired in Pla2g5-null mice exposed to *Alternaria*. However adoptive transfers of macrophages restored ILC2 activation by a mechanism that is at least in part dependent on Pla2g5-dependent production of IL-33, LA and OA, which sustain ILC2 activation in vitro and in vivo, and on Pla2g5-dependent expression of the LA-preferring FFA receptor-1 (FFAR1) by ILC2s.

It is now well established that ILC2 are key effectors of pulmonary inflammation. Their contribution is particularly evident in models triggered by the release of alarmins (IL-33, IL-25, TSLP) from epithelial cells[2, 4, 9, 11, 38, 39] in response to environmental proteases[11], many of which are relevant to asthma in humans[13]. IL-33, alone and in combination with IL-25, TSLP, and other cytokines can directly induce IL-5, IL-13, and IL-9 generation from ILC2s, promoting eosinophilic inflammation and goblet cell metaplasia that can occur independently of or in concert with adaptive immunity. The *Alternaria* model of pulmonary inflammation has been particularly useful to establish the contribution of innate, epithelial-derived alarmins and their downstream effects on ILC2 activation and subsequent development of airway inflammation[1, 3]. While macrophages can also express IL-33[40], and other innate cell types have been proposed to interact with ILC2[41], no previous studies had established whether macrophages can activate ILC2 in *Alternaria*-induced pulmonary inflammation and which mediators might be involved. Pla2g5-null mice show markedly impaired type 2 pulmonary inflammation that reflects, at least in part, a requirement for cell-intrinsic Pla2g5 for macrophage effector functions[25, 26]. We therefore investigated the role of Pla2g5 in general and macrophage-associated Pla2g5 in particular, in lipid-generating function and its potential downstream effects on ILC2 activation in a model of pulmonary inflammation induced by *Alternaria*.

Figure 1C:
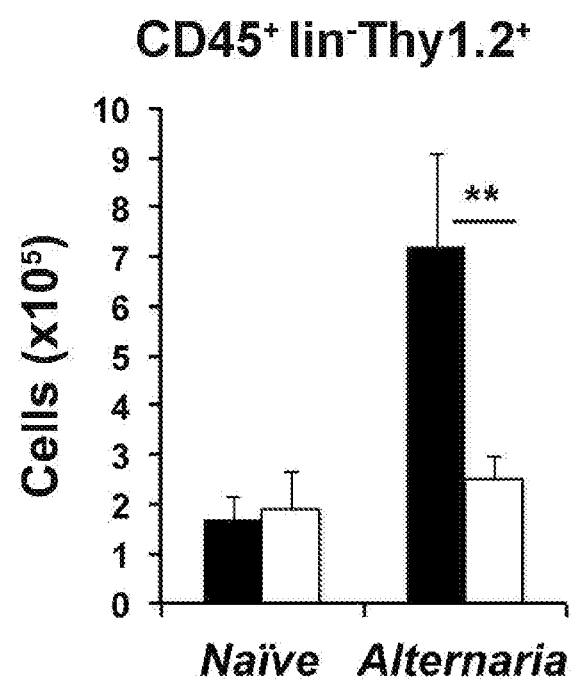
Figure 1D:
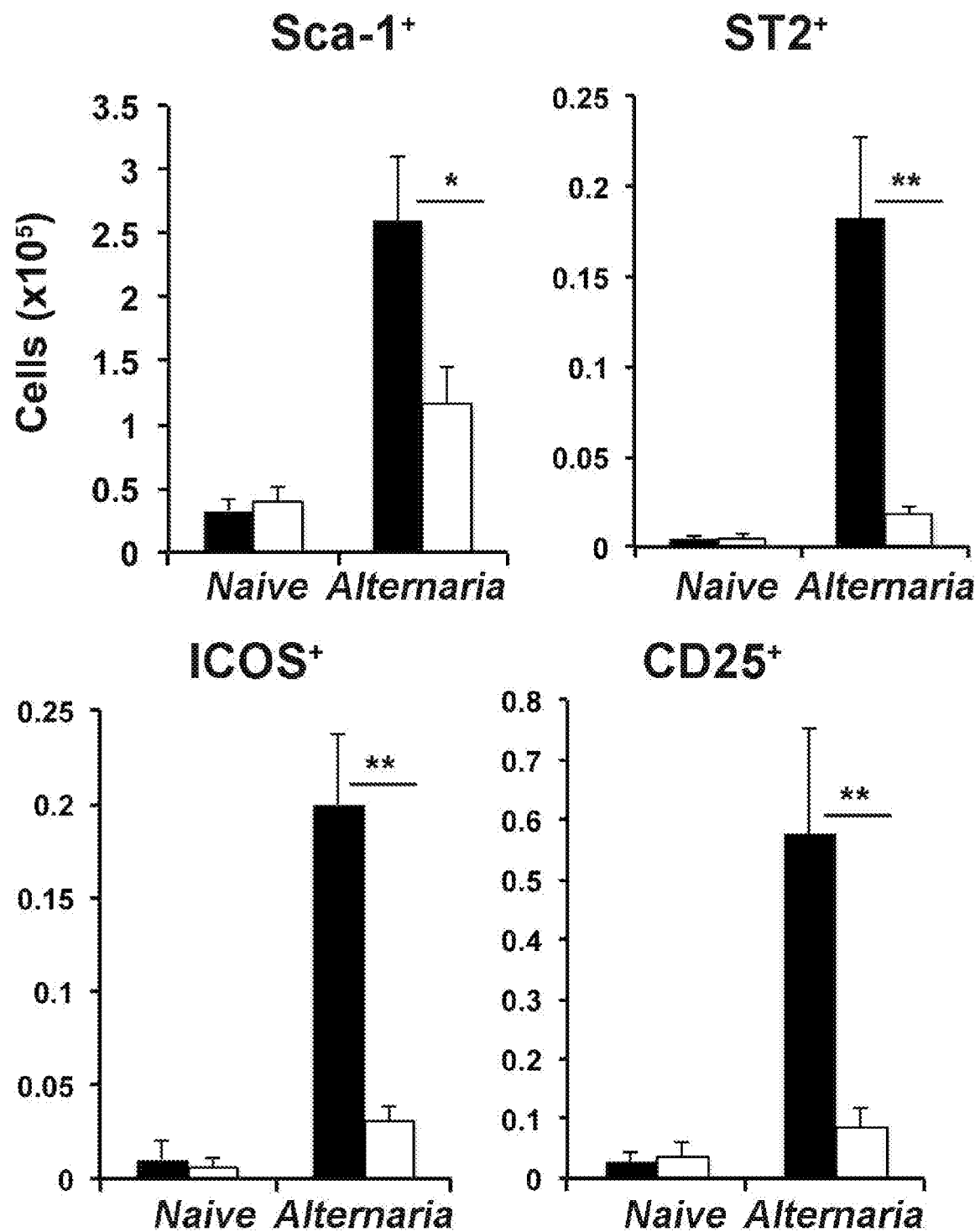
Figure 1E:
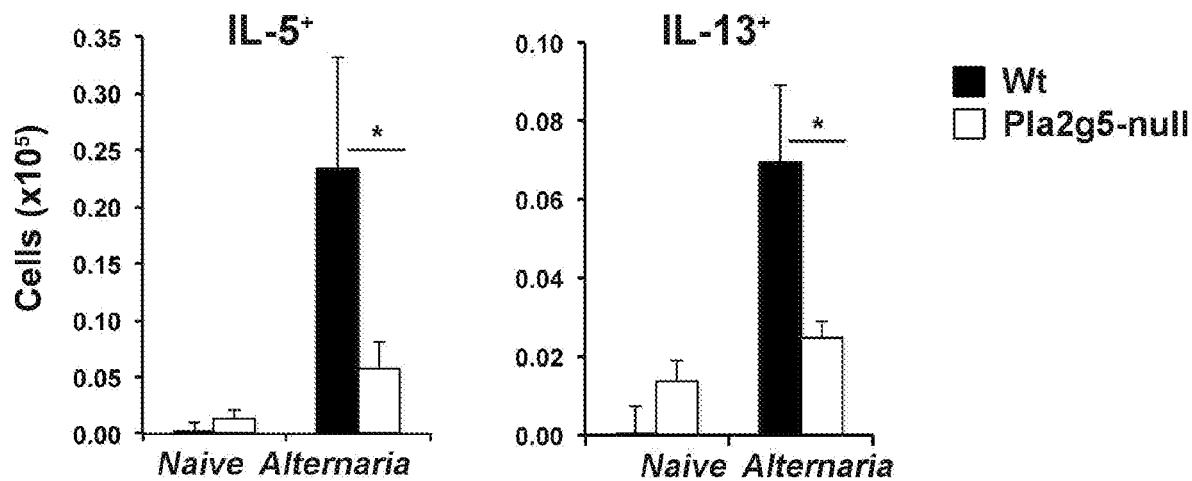
Figure 2A:
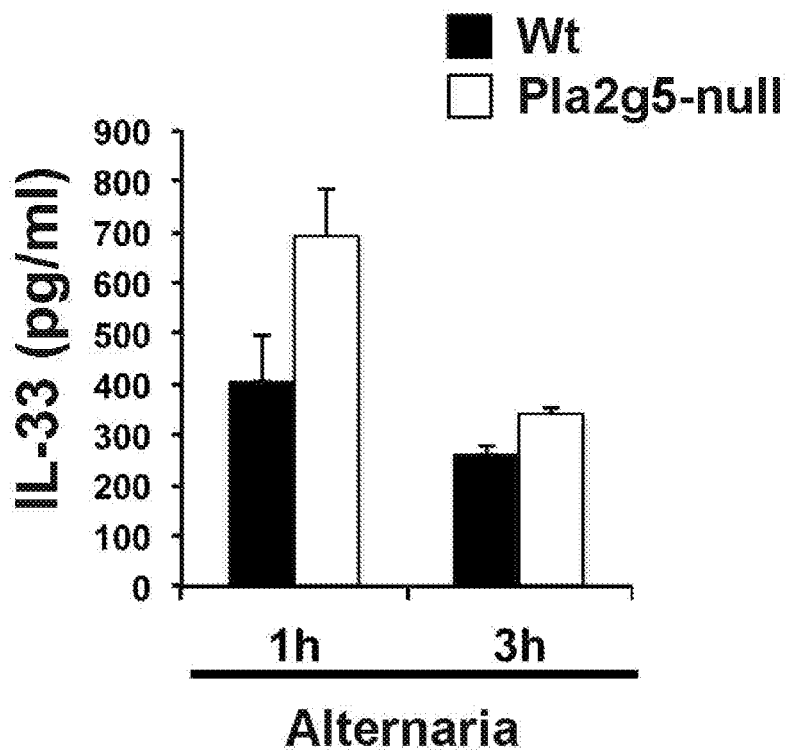
FIGS. 2A-E. Induced IL-33 generation in the lung requires Pla2g5. (A) IL-33 levels determined by ELISA of BAL 1 or 3 hours after *Alternaria* administration in Wt and Pla2g5-null mice. (B) Expression of IL-33 protein by Western blot in homogenate lungs of naïve and *Alternaria*-treated Wt and Pla2g5-null mice treated with *Alternaria* for 10 days. Equivalent loading was confirmed by immunoblot analysis for β-actin. (C) Frozen sections from the lungs of Wt and Pla2g5-null mice naïve or treated with *Alternaria* for 10 days, were stained for IL-33 (red), SPC (green) and nuclei (blue). Original magnification ×40. Size bar 50 μm. (D) Expression of IL-33 on gated CD68+ lung cells of naïve and *Alternaria*-treated Wt and Pla2g5-null mice evaluated by flow cytometry. (E) Expression of IL-33 mRNA in Wt and Pla2g5-null BM-macrophages. Expression of IL-33 mRNA relative to GAPDH measured by qPCR in BM-macrophages unstimulated or stimulated with GM-CSF, IL-33, IL-4. Data are from one experiment representative of two independent experiments. (A and D) Values are mean±SEM from two or three independent experiments with 5-8 mice per group. (B and C) Images and panels are from one experiment representative of two with similar results. *P<0.05.

Wt and Pla2g5-null mice were subjected to a protocol involving the administration of *Alternaria* four times over a 10-day period, which elicits prominent contributions from IL-33 and ILC2s. The marked pulmonary eosinophilia and increases in the numbers of total and activated ILC2s observed in Wt mice (FIGS. 1A-E) were all sharply reduced in Pla2g5-null mice. The reduced levels of both eosinophils and ILC2s were paralleled by reduced levels of IL-33 induction (FIG. 2B), but not constitutively levels of IL-33 (FIG. 2B), or by release of IL-33 in response to a single *Alternaria* dose (FIG. 2A). AT2 cells are the dominant source of pre-formed IL-33 in the mouse lung, as well as of the pre-formed IL-33 in response to a single dose of *Alternaria*[15]. In our study, AT2 cells showed equivalent staining for IL-33 in Wt and Pla2g5-null mice (FIG. 2C), suggesting that Pla2g5 functions are not required by AT2 to store or release IL-33. In marked contrast, IL-33 expression by lung macrophages was substantially induced in *Alternaria*-treated Wt mice but not in Pla2g5-null mice (FIG. 2D), suggesting that macrophages may be one of the cell types accounting for the impaired induction of IL-33 in Pla2g5-null lungs. Our previous studies demonstrated that macrophage-intrinsic Pla2g5 was necessary for inducible expression of Th2 cell-active chemokines[25]. Our current results, supported by our ex vivo data (FIG. 2E), suggest that this may also be the case for IL-33 induction.

Figure 3A:
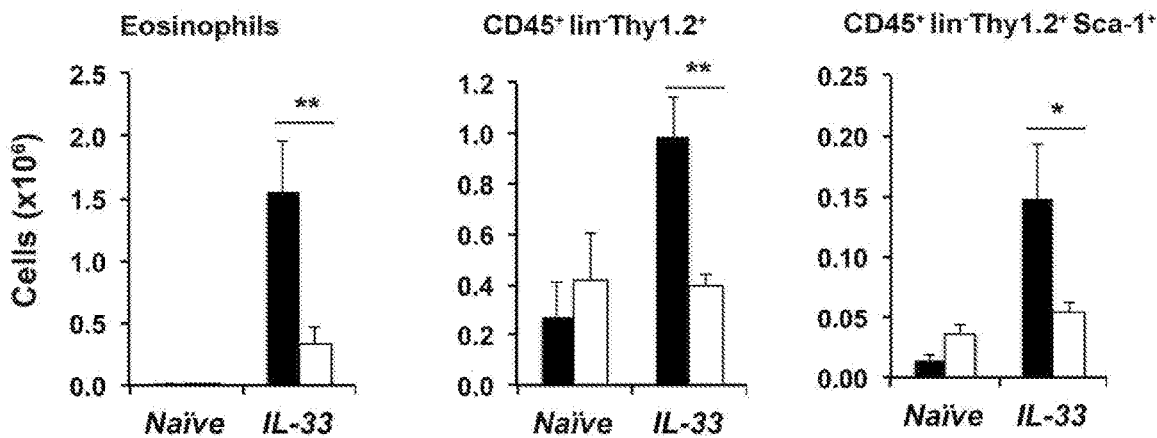
FIGS. 3A-B. r-IL-33 induces pulmonary inflammation in Wt but not in Pla2g5-null mice. (A) Flow cytometry analysis of eosinophils, ILC2 and ILC2 expressing Sca-1, (B) Relm-α expression on gated CD45+CD11c+ cells from homogenate lungs of Wt and Pla2g5-null mice naïve or administered r-IL-33 for 10 days. Values are mean±SEM of two (B) or three (A) independent experiments with 7-15 mice per group. **P<0.005, *P<0.05.
Figure 3B:
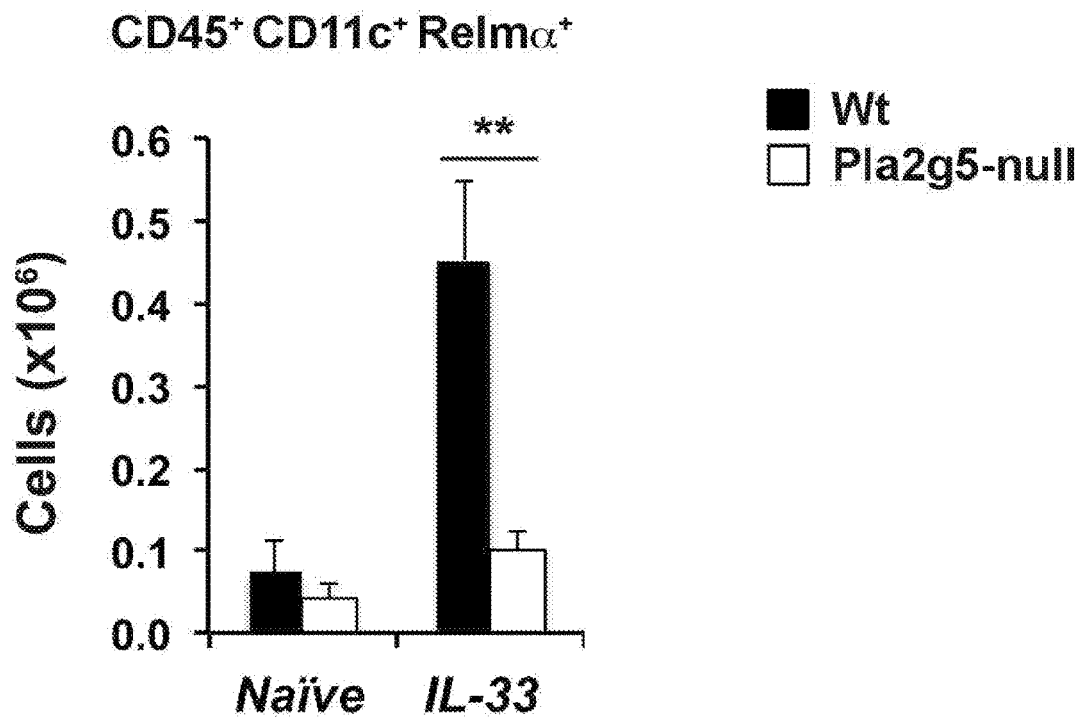
Figure 4A:
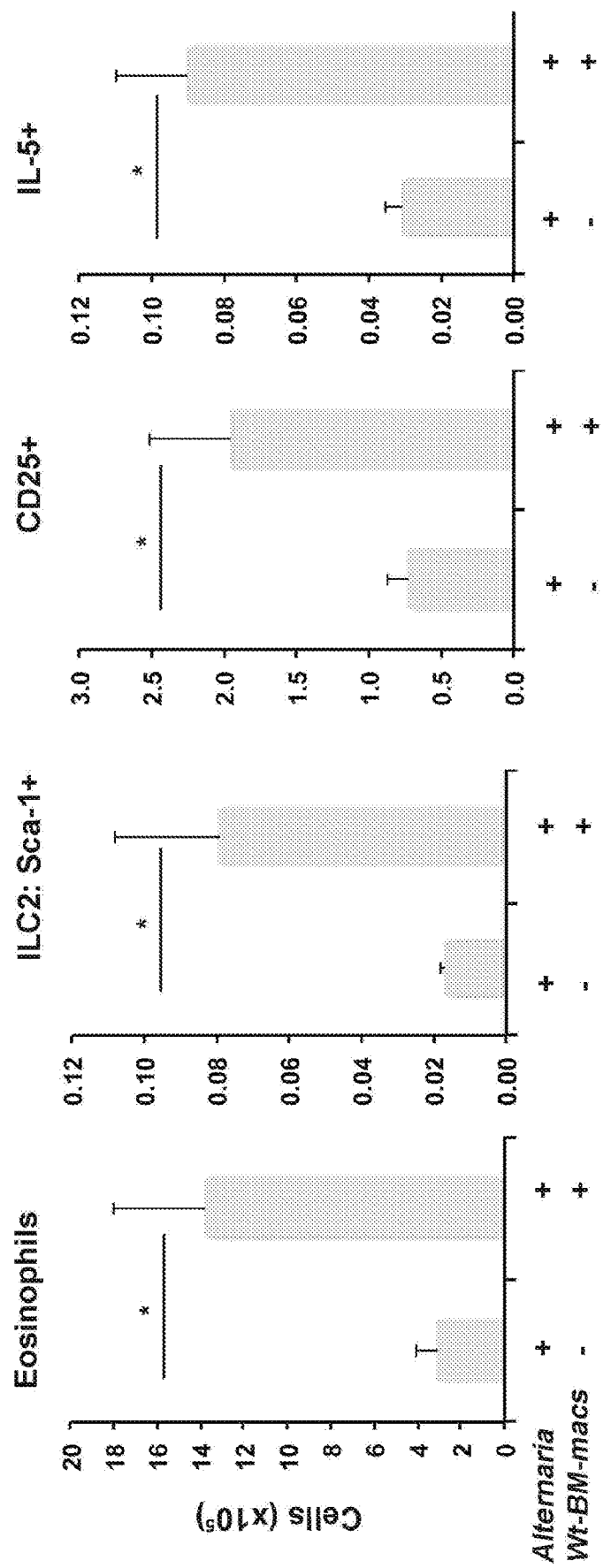
FIGS. 4A-B. Transfer of Wt BM-macrophages into Pla2g5-null recipient mice restores *Alternaria*-induced pulmonary inflammation. Pla2g5-null (A) and Wt (B) recipient mice received Wt BM-macs intratracheally at day 2, followed by *Alternaria* intranasally at day 3, 6 and 9 or only *Alternaria*. Mice were euthanized 18 hours after the last dose. Analysis by flow cytometry of eosinophils gated as CD45+ CD11c− SiglecF+ lung cells and expression of CD25, Sca1 and intracellular IL-5 on ILC2 gated as CD45+ Lin− Thy1.2+ lung cells. Values are mean±SEM of 4 independent experiments with 13-23 mice per group. *P<0.05.
Figure 5A:
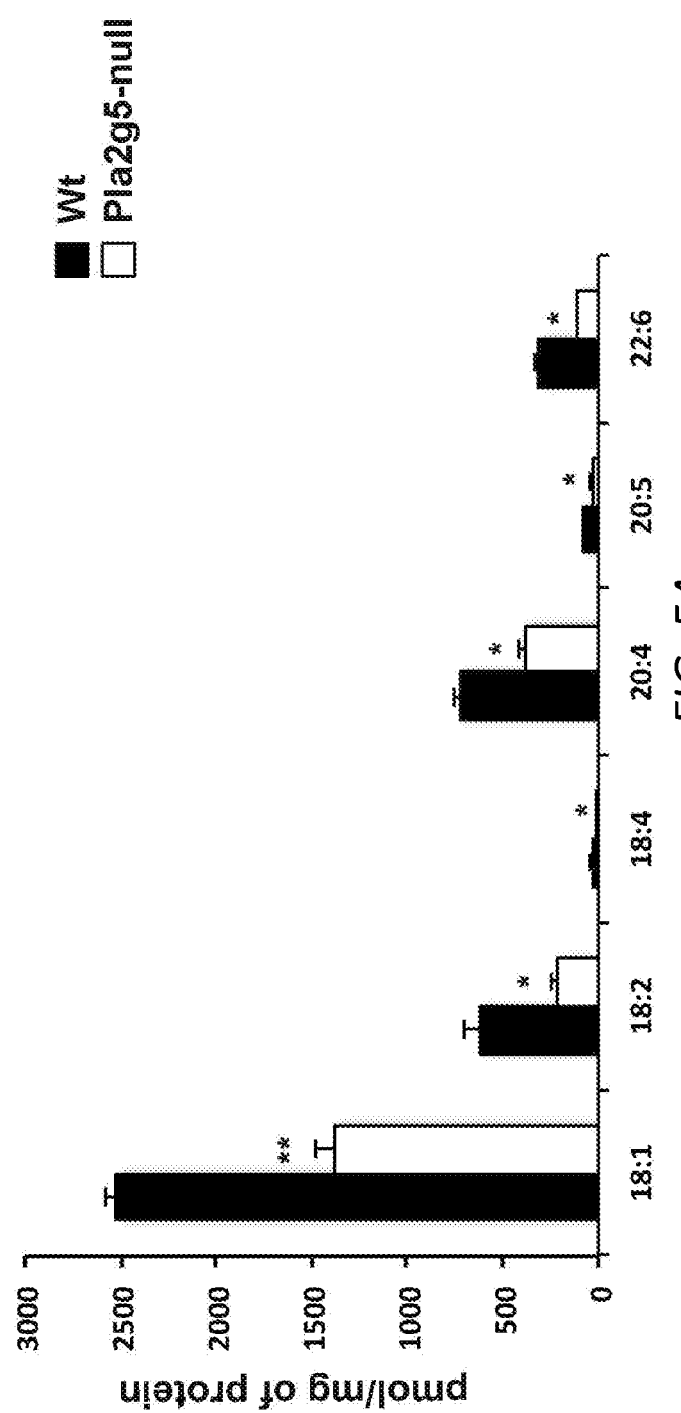
FIGS. 5A-C. Intranasal administration of LA and OA in combination with r-IL-33 increased eosinophilia and ILC2 activation in Wt and Pla2g5-null mice. (A) Production of FFAs measured by mass spectrometry in Wt and Pla2g5-null BM-Macrophages. Flow cytometry analysis of (B) numbers of eosinophils and (C) ILC2s expressing of intracellular IL-5 in homogenate lungs of Wt (black bars) and Pla2g5-null mice (white bars) treated intranasally with IL-33, LA or OA as indicated. (A) Data are from 3 independent experiments. Values are expressed as means±SEM and were compared by t-test. (B, C) Values are mean±SEM of two-four independent experiments with 4-12 mice per group, and were compared by One-way ANOVA with Sidak's correction for multiple comparisons. **P<0.005, *P<0.05.
Figure 5B:
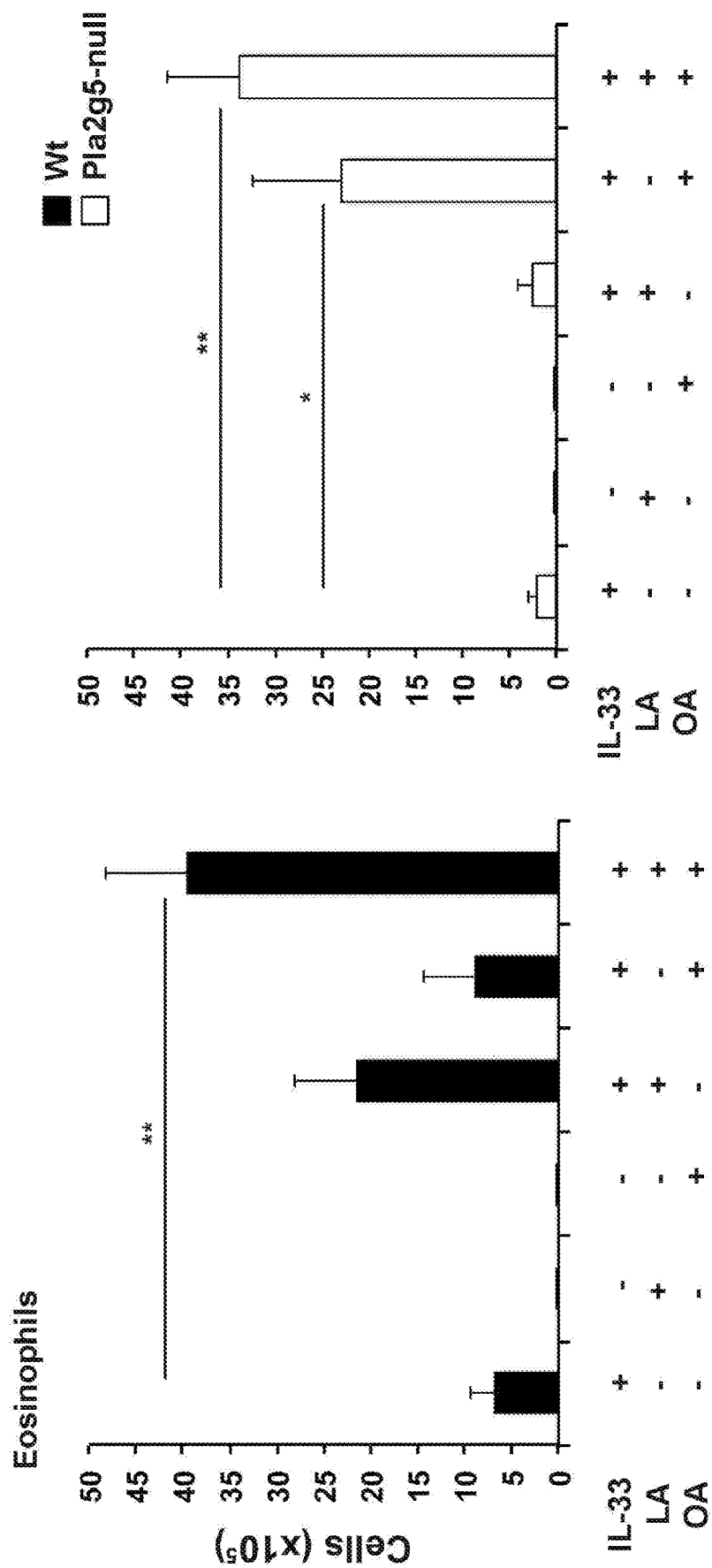
Figure 5C:
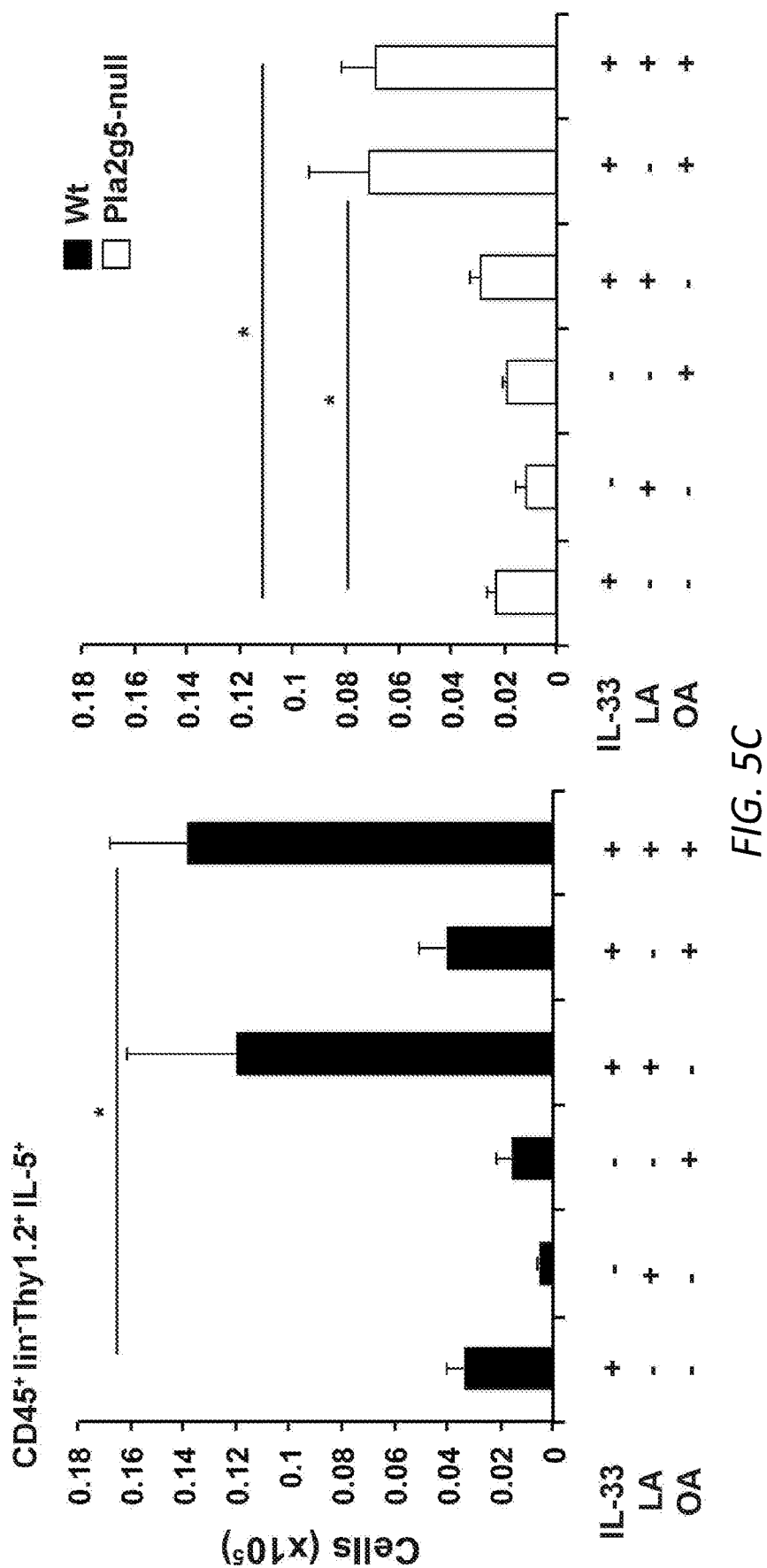
Figures 6A, 6B:
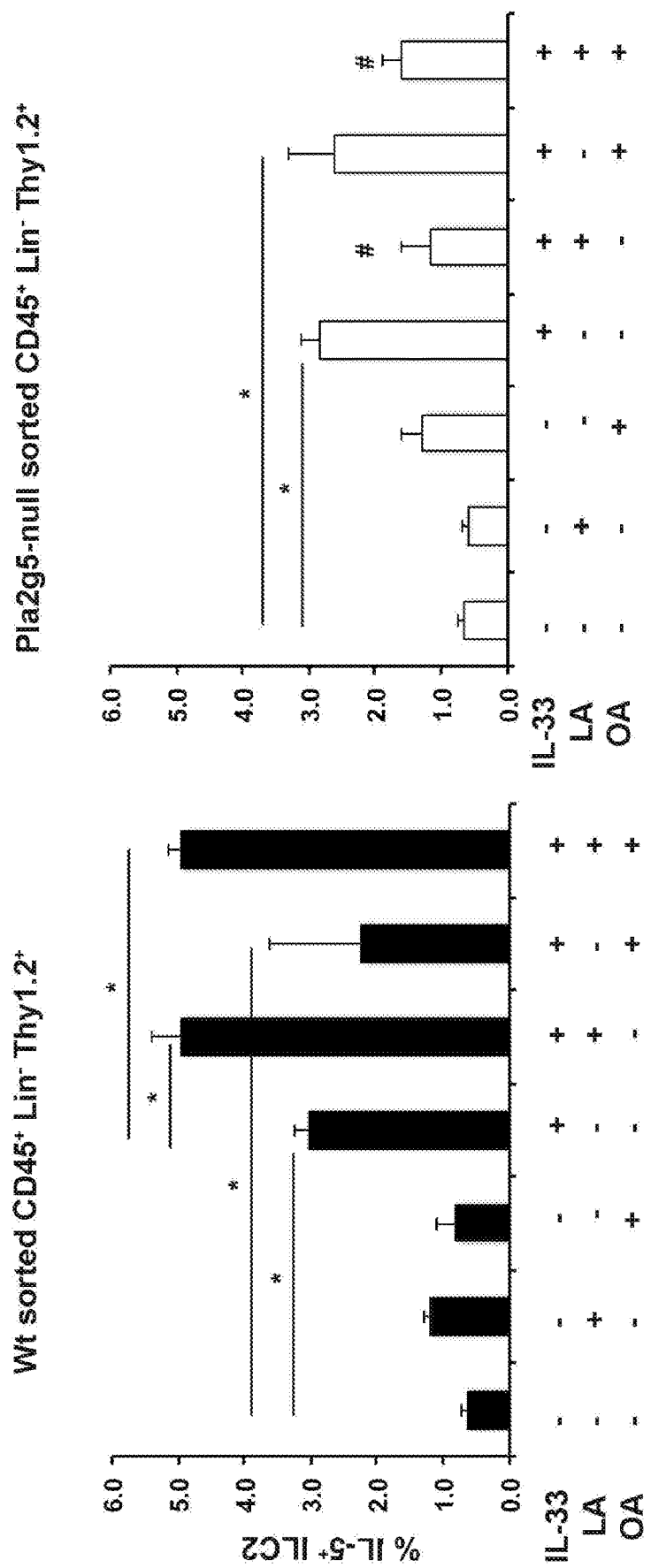
FIGS. 6A-C. Differential LA- and OA-induced activation of sorted Wt and Pla2g5-null ILC2 and FFAR1 expression. ILC2s expanded in-vivo by 4 *Alternaria* challenges for 10 days followed by FACS sorting, were rested for 40 hours prior to in-vitro stimulation with LA (200 μM), OA (200 μM), IL-33 (30 ng/ml) or all together for 8 hours then analyzed by flow cytometry for % of IL-5 positive Wt (A) and Pla2g5-null (B) ILC2. (C) Expression of FFAR1 and FFAR4 mRNA relative to GAPDH measured by qPCR in sorted ILC2s from *Alternaria*-treated Wt and Pla2g5-null mice. Data are from at least 3 independent experiments. Values are expressed as means±SEM and were compared by One-way ANOVA with Sidak's correction for multiple comparisons (A-B) or t-test (C). *P<0.05, #P<0.05 vs. IL-33 alone.

When administered exogenously to I Wt mice, r-IL-33 is sufficient alone to drive a robust type 2 inflammatory response that depends on ILC2[3, 38]. Despite the evident role of Pla2g5 in IL-33 induction by macrophages, the direct administration of IL-33 to I Pla2g5-null mice was insufficient to induce inflammation, ILC2 expansion, and macrophage activation (FIGS. 3A-B). Combined with the fact that transfer of Wt macrophages almost fully restored these parameters in Pla2g5-null mice in response to *Alternaria* challenges (FIG. 4A), we suspected the involvement of additional Pla2g5-dependent factors that could enable macrophages to activate ILC2, alone or in concert with IL-33. We identified two candidate FFAs (LA and OA) as Pla2g5-dependent factors derived from macrophages (FIG. 5A). Both of these FFAs can signal to immune and non-immune cells through the GPCRs FFAR1 and FFAR4, although their potential roles as mediators of allergic inflammation in general and stimulants of ILC2 activation in particular had not been explored. The sharp potentiation of IL-33-driven eosinophilic inflammation and ILC2 expansion in Wt mice by LA, alone and in combination with OA (FIGS. 5B and C), was parallel by its effects on IL-33-induced IL-5 generation by ILC2 ex vivo (FIG. 6A). In contrast, the impaired response of Pla2g5-null ILC2 to LA in vivo (FIG. 5C) and in vitro (FIG. 6B) is consistent with the loss of FFAR1 (FIG. 6C), which exhibits a preference for LA over to OA[42]. Notably, although unable to directly activate Wt or Pla2g5-null ILC2s, OA did substantially enhance IL-33-induced eosinophilic inflammation and expand lung ILC2s in Pla2g5-null mice, reflecting a compensatory mechanism. Since FFAR1 and FFAR4 are broadly expressed by immune and non-immune cell types[43], it is likely that Pla2g5-derived FFAs potentiate innate type 2 immune responses and ILC2 activation by both direct and indirect pathways. We speculate that ILC2s require conditioning in vivo by one or more inductive factors that are deficient in Pla2g5-null mice in order to express FFAR1 and respond to LA. Importantly, the absence of Pla2g5 in macrophages (FIG. 7) seems sufficient to suppress pulmonary inflammation, through yet to be defined pathways.

Our data clearly identify a role for macrophages, and Pla2g5-derived FFAs, as activators of ILC2, acting in concert with IL-33. It is likely that the coordinate action of ILC2, macrophages and epithelial cells induces pulmonary inflammation, highlighting a complex interplay of innate cells in the lung[4, 12, 44]. These data also suggest that FFAs directly activate ILC2 through FFAR1 expressed on ILC2 in a Pla2g5-dependent fashion. Thus, our observations suggest that macrophage-derived FFAs amplify innate, IL-33-triggered type 2 immunopathology in diseases such as asthma. We speculate that LA, derived at least in part from Pla2g5-expressing macrophages, may contribute to the function of ILC2s in other circumstances, such as homeostasis of adipose tissue and glucose metabolism where macrophages, Pla2g5, IL-33, and ILC2 have all been implicated[22, 45].

Methods of Treatment

The methods described herein include methods for the treatment of disorders associated with inflammation, e.g., pulmonary inflammation. In some embodiments, the disorder is asthma. Generally, the methods include administering a therapeutically effective amount of autologous macrophages lacking Pla2g5 as described herein, to a subject who is in need of, or who has been determined to be in need of, such treatment. In some embodiments, the methods include administering at least 0.5 million, 1 million, 2 million, or 4 million, or more, e.g., 0.25 to 5 million cells.

As used in this context, to "treat" means to ameliorate at least one symptom of the disorder associated with pulmonary inflammation. Often, pulmonary inflammation results in breathlessness, wheezing and a variable airflow obstruction; thus, a treatment can result in a reduction in breathlessness, wheezing and a variable airflow obstruction and a return or approach to normal breathing. Administration of a therapeutically effective amount of a treatment described herein will result in decreased levels of pulmonary inflammation.

Asthma

A variety of cellular inflammatory phenotypes is associated with asthma, and airway hyper-responsiveness (AHR), an increase in responsiveness of the conducting airways, is characteristic. Symptoms include breathlessness, wheezing and a variable airflow obstruction. A diagnosis of asthma can be made by a healthcare provider using standard diagnostic methods, e.g., following the Guidelines for the Diagnosis and Management of Asthma (EPR-3) (2007), including a subject history of coughing, recurrent wheezing, recurrent difficulty breathing, and recurrent chest tightness, that may occur or worsen at night or with exercise, viral infection, exposure to allergens and irritants, changes in weather, hard laughing or crying, stress, or other factors. Spirometry or imaging methods can be used to determine that airway obstruction is at least partially reversible. See, e.g., Murdoch and Lloyd, Mutat Res. 2010 Aug. 7; 690(1-2): 24-39.

Pla2g5-Deficient Suppressive Macrophages

The present methods include the administration of Pla2g5-deficient suppressive macrophages, preferably autologous macrophages. As used herein, the term "Pla2g5-deficient suppressive macrophages" refers to macrophages in which Pla2g5 expression levels have been artificially decreased by at least 70%, to no more than 30% of normal levels, or decreased by at least 75%, 80%, 90%, or 95% or more. The methods can include obtaining peripheral blood from a subject with asthma (i.e., a subject to be treated using a method described herein), and isolating monocytes from the sample to provide an enriched sample of monocytes (CD14+). In some embodiments, magnetic activated cell sorting (MACS), e.g., positive or negative selection, is used, e.g., with a commercially available kit (Monocyte Isolation Kit II, human, Miltenyi Biotec), wherein non-monocyte cells are indirectly magnetically labeled using a cocktail of biotin-conjugated antibodies as well as anti-biotin beads; highly enriched unlabeled monocytes are obtained by depletion of the magnetically labeled cells. Other methods can also be used, e.g., percoll gradients (de Almeida e al., Mem Inst Oswaldo Cruz, Rio de Janeiro, Vol. 95(2): 221-223, March/April 2000); positive selection of monocytes by anti-CD14-coated microbeads (Elkord et al., Immunology. 2005 February; 114(2): 204-212; Monocyte Isolate Kit with CD14 MicroBeads, Miltenyi biotec); plate-adherence isolation (Elkord et al., Immunology. 2005 February; 114(2): 204-212, Freundlich and Avdalovic. 1983. J. Immunol. Methods 62: 31-37); double density gradient centrifugation (Menck et al., J. Vis. Exp. (91), e51554, doi:10.3791/51554 (2014)); or RosetteSep antibody cocktail (this antibody cocktail crosslinks unwanted cells to red blood cells (RBCs), forming rosettes. The unwanted cells then pellet with the free RBCs when centrifuged over a density centrifugation medium (e.g., Ficoll-Paque™ PLUS, Lymphoprep™; Stemcell Technologies, France). Ficoll-Paque PLUS is a sterile, ready to use density gradient medium for purifying lymphocytes in high yield and purity from small or large volumes of human peripheral blood, using a simple and rapid centrifugation procedure based on the method developed by Bøyum et al., Scand J Clin Lab Invest 21 Suppl, 97, 77-89 (1968). It is an aqueous solution of density 1.077+0.001 g/ml containing 5.7 g Ficoll 400 and 9 g sodium diatrizoate with 0.0231 g calcium disodium ethylenediamintetraacetic acid in every 100 ml. Ficoll 400 is a synthetic high molecular weight (Mw 400 000) polymer of sucrose and epichlorohydrin that is readily soluble in water. Ficoll 400 molecules are highly branched, approximately spherical, and compactly coiled with a Stokes' radius of approximately 10 nm.

The monocytes are then derived into macrophages, e.g., using a suitable protocol, a number of which are known in the art. See, e.g., below and Yamaguchi et al., J L B 2016; Menck et al., J. Vis. Exp. (91), e51554 (2014); Ohradanova-Repic et al., Clinical & Translational Immunology (2016) 5, e55; Mia et al., Scand J Immunol. 2014 May; 79(5):305-14). In preferred embodiments, the methods include incubating the cells in the presence of recombinant human GM-CSF for 7-14 or 12-14 days, preferably 13 days, which induces expression of the generic macrophage marker CD64. Alternatively, macrophage colony-stimulating factor (M-CSF) for about 7 days can be used (see Ohta et al., Journal of immunology 2013; 190(12): 5927-5938).

Then, the macrophages are converted into suppressive macrophages by reducing the expression of Pla2g5 using an inhibitory nucleic acid to knock down the protein, e.g., using siRNA, shRNA, antisense, or CRISPR/Cas9 targeting Pla2g5. The cells are maintained in media comprising the inhibitory nucleic acid for about 12-36 hours, e.g., about 24 hours, preferably followed by 24 hours in GM-CSF-containing medium.

This is followed by treatment with IL-4, e.g., for 6-48 hours or so, for M2 activation; expression of CCL2 and TGM2 is increased in the M2 cells after IL-4 treatment. In the Pla2g5 knock-out macrophages, CCL22 and TGM2 expression is also reduced as compared to wild type cells exposed to the same protocol. Note that Pla2g5 and TGM2 are enzymes and the enzymatic activity is reduced for both enzymes after knocking down Pla2g5. These differences could be explained by the transient removal of Pla2g5 in human cells.

The cells can optionally be purified as needed to provide a population comprising at least 80% Pla2g5-deficient suppressive macrophages, e.g., at least 85%, 90%, 95%, or 99% pure Pla2g5-deficient suppressive macrophages, and/or allowed to proliferate, to provide at least 0.5 million, 1 million, 2 million, or 4 million, or more, e.g., 0.25 to 5 million cells.

Figure 7A:
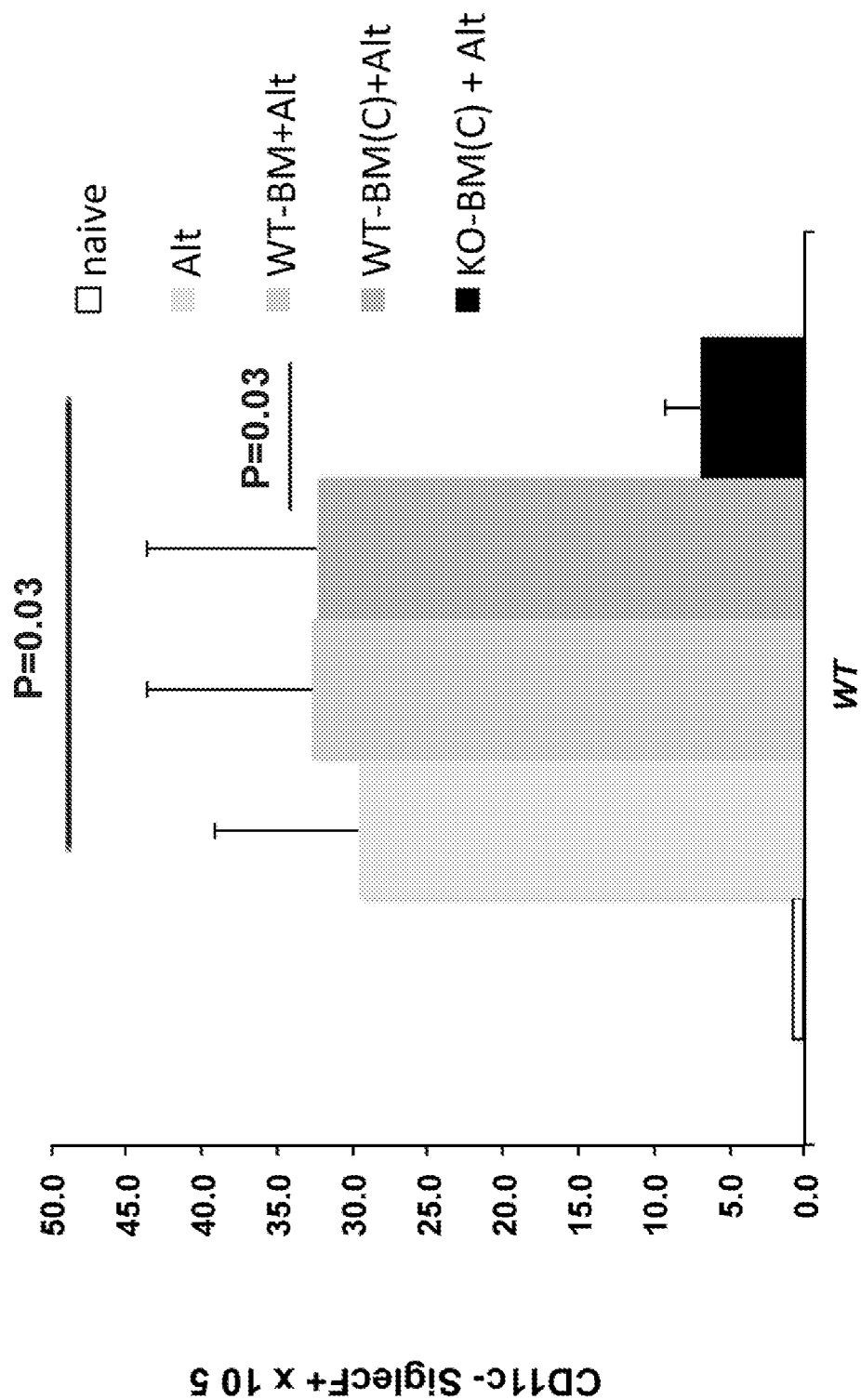
FIGS. 7A-B. Transfer of Pla2g5-null BM-macrophages into Wt recipient mice suppresses *Alternaria*-induced pulmonary inflammation. Wt recipient mice received *Alternaria* (light grey bars), Wt BM-Macrophages (medium grey bars), Wt BM-macrophages activated by a cocktail of cytokines (IL-4, GM-CSF, IL33 (BMI) (dark gray bars), or Pla2g5-null BM-macs (black bars) intratracheally at day 2, followed by *Alternaria* intranasally at day 3, 6 and 9 or only *Alternaria*. Mice were euthanized 18 hours after the last dose. Analysis by flow cytometry of eosinophils gated as CD45+ CD11c− SiglecF+ lung cells (A) and expression of intracellular IL-5 on ILC2 gated as CD45+ Lin− Thy1.2+ lung cells (B). Values are mean±SEM of 3 independent experiments with 12-13 mice per group. *P<0.05.
Figure 7B:
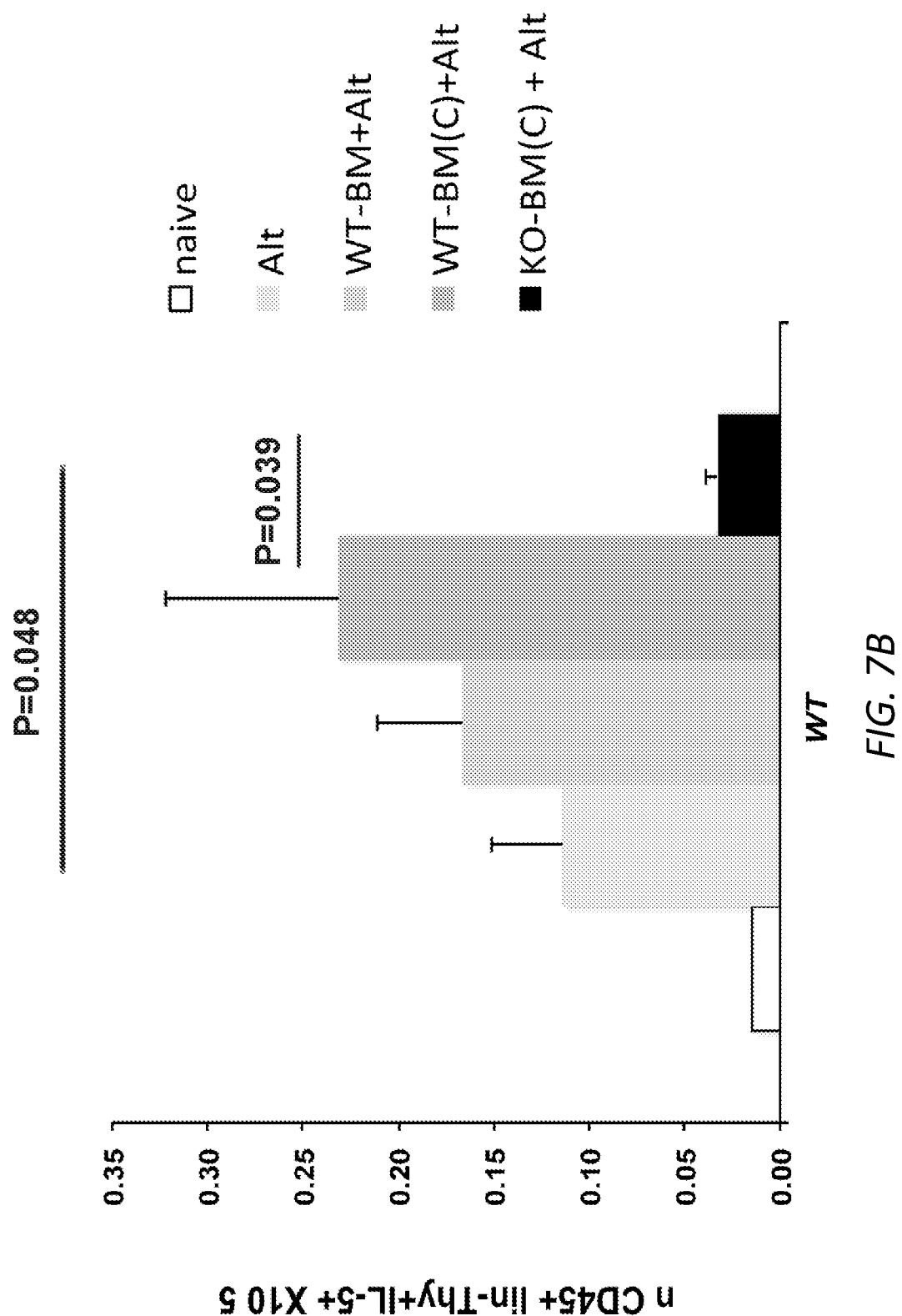

The final step would be to re-introduce Pla2g5-null macrophages into the airways of patients with asthma to obtain suppression/reduction of inflammation and therefore asthma, as demonstrated by the in vivo mouse experiments (FIGS. 7A and 7B below).

Pla2g5 Inhibitory Nucleic Acids

Inhibitory nucleic acids useful in the present methods and compositions include CRISPR guide RNAs (used in conjunction with a CRISPR/Cas9 protein) antisense oligonucleotides, single- or double-stranded RNA interference (RNAi) compounds such as siRNA or shRNA compounds, compounds with modified bases such as locked nucleic acids (LNAs), peptide nucleic acids (PNAs), ribozymes, gapmers, mixmers, and other oligomeric compounds or oligonucleotide mimetics that hybridize to at least a portion of the target Pla2g5 nucleic acid and modulate its function to reduce expression of Pla2g5 protein. Reference sequences for human Pla2g5 can be found in GenBank at NM 000929.2 (nucleic acid) and NP 000920.1 (protein).

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range there within. Suitable sequences can be identified, e.g., using computational and/or "gene walk" methods. To design and to optimize the inhibitory activity of the inhibitory nucleic acids; for example, a series of oligonucleotides of 10-30 nucleotides spanning the length of a target nucleic acid can be prepared, followed by testing for activity. Optionally, gaps, e.g., of 5-10 nucleotides or more, can be left between the inhibitory nucleic acids to reduce the number of oligonucleotides synthesized and tested. GC content is preferably between about 30 60%.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA, LNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers (chimeric antisense oligonucleotide that contains a central block of deoxynucleotide monomers sufficiently long to induce Rnase H cleavage), as well as mixmers (oligomers comprising alternating short stretches of LNA and DNA). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 8,604,192; 8,697,663; 8,703,728; 8,796,437; 8,865,677; and 8,883,752 each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH,); amide backbones (De Mesmaeker (1995) Ace. Chem. Res. 28:366-374); morpholino backbone structures (Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, Nielsen (1991) Science 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, phosphonoacetate phosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey (2002) Biochemistry 41(14), 4503-4510); Genesis, volume 30, issue 3, 2001; Heasman, (2002) Dev. Biol. 243, 209-214; Nasevicius (2000) Nat. Genet. 26, 216-220; Lacerra (2000) Proc. Natl. Acad. Sci. 97, 9591-9596; and U.S. Pat. No. 5,034,506, issued Jul. 23, 1991. Cyclohexenyl nucleic acid oligonucleotide mimetics are described in Wang (2000) Am. Chem. Soc. 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,677,439; and 8,927,513 each of which is herein incorporated by reference.

One or more substituted sugar moieties can also be included, e.g., one of the following at the 2' position: OH, SH, SCH$_3$, F, OCN, OCH$_3$, OCH$_3$O(CH$_2$)nCH$_3$, O(CH$_2$)nNH$_2$ or O(CH$_2$)nCH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the haracterization properties of an oligonucleotide and other substituents having similar properties. A preferred modification includes 2'-methoxyethoxy [2'-0-CH$_2$CH$_2$OCH$_3$, also known as 2'-O-(2-methoxyethyl)] (Martin (1995) Helv. Chim. Acta 78, 486). Other preferred modifications include 2'-methoxy (2'-0-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, 2,6-diaminopurine; 5-ribosyluracil (Carlile (2014) Nature 515 (7525): 143-6). Kornberg, A., DNA Replication, W. H. Freeman & Co., San Francisco, 1980, pp 75-77; Gebeyehu (1987) Nucl. Acids Res. 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide. In some embodiments, both the nucleobase and backbone may be modified to enhance stability and activity (El-Sagheer (2014) Chem Sci 5:253-259).

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen (1991) Science 254, 1497-1500; and Shi (2015).

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science and Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger (1989) Proc. Natl. Acad. Sci. USA 86, 6553-6556), cholic acid (Manoharan (1994) Bioorg. Med. Chem. Let. 4, 1053-1060), a thioether, e.g., hexyl-S-tritylthiol (Manoharan (1992) Ann. N. Y. Acad. Sci. 660, 306-309; Manoharan (1993) Bioorg. Med. Chem. Let. 3, 2765-2770), a thiocholesterol (Oberhauser (1992) Nucl. Acids Res. 20, 533-538), an aliphatic chain, e.g., dodecandiol or undecyl residues (Kabanov (1990) FEBS Lett. 259, 327-330; Svinarchuk (1993) Biochimie 75, 49-54), a phospholipid, e.g., di-hexadecyl-rac-glycerol or triethylammonium 1,2-di-O-hexadecyl-rac-glycero-3-H-phosphonate (Manoharan (1995) Tetrahedron Lett. 36, 3651-3654; Shea (1990) Nucl. Acids Res. 18, 3777-3783), a polyamine or a polyethylene glycol chain (Mancharan (1995) Nucleosides & Nucleotides 14, 969-973), or haracteri acetic acid (Manoharan (1995) Tetrahedron Lett. 36, 3651-3654), a palmityl moiety (Mishra (1995) Biochim. Biophys. Acta 1264, 229-237), or an octadecylamine or hexylamino-carbonyl-t oxycholesterol moiety (Crooke (1996) J. Pharmacol. Exp. Ther. 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941, 8,865,677; 8,877,917 each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the haracterization properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the haracterization properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or haracteri acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target nucleic acid, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a nucleic acid, then the bases are considered to be complementary to each other at that position. 100% complementarity is not required.

In some embodiments, the location on a target nucleic acid to which an inhibitory nucleic acid hybridizes is defined as a target region to which a protein binding partner binds. These regions can be identified by reviewing the data submitted herewith in Appendix I and identifying regions that are enriched in the dataset; these regions are likely to include the protein binding sequences. Routine methods can be used to design an inhibitory nucleic acid that binds to this sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly, preferred target segments are represented by RNA sequences that comprise at least the 5 consecutive nucleotides from the 3'-terminus of one of the illustrative preferred target segments (the remaining nucleotides being a consecutive stretch of the same nucleic acid beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

Making and Using Inhibitory Nucleic Acids

The inhibitory nucleic acids used to practice the methods described herein, whether RNA, cDNA, genomic DNA, vectors, viruses or hybrids thereof, can be isolated from a variety of sources, genetically engineered, amplified, and/or expressed, generated recombinantly or synthetically by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; Maier (2000) Org Lett 2(13): 1819-1822; Egeland (2005) Nucleic Acids Res 33(14):e125; Krotz (2005) Pharm Dev Technol 10(2):283-90 U.S. Pat. No. 4,458,066. Recombinant nucleic acid sequences can be individually isolated or cloned and tested for a desired activity. Any recombinant expression system can be used, including e.g. in vitro bacterial, fungal, mammalian, yeast, insect or plant cell expression systems.

Alternatively, recombinantly produced Pla2g5 inhibitory nucleic acids can be used. Nucleic acid sequences encoding a Pla2g5 inhibitory nucleic acid can be inserted into delivery vectors and expressed from transcription units within the vectors, e.g., in host cells. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion or "seamless cloning", ligation, transformation, plasmid purification, and DNA sequencing, for example as described in Sambrook et al. "Molecular Cloning: A Laboratory Manual." (1989)), Coffin et al. (Retroviruses. (1997)) and "RNA Viruses: A Practical Approach" (Alan J. Cann, Ed., Oxford University Press, (2000)). "Seamless cloning" allows joining of multiple fragments of nucleic acids in a single, isothermal reaction (Gibson (2009) Nat Methods 6:343-345; Werner (2012) Bioeng Bugs 3:38-43; Sanjana (2012) Nat Protoc 7:171-192). As will be apparent to one of ordinary skill in the art, a variety of suitable vectors are available for transferring nucleic acids encoding Pla2g5 inhibitory nucleic acids into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids encoding Pla2g5 inhibitory nucleic acids can be constructed based on viral backbones including, but not limited to, a retrovirus, lentivirus, adenovirus, adeno-associated virus, pox virus or alphavirus (Warnock (2011) Methods in Molecular Biology 737:1-25). The recombinant vectors capable of expressing the nucleic acids can be delivered as described herein, and persist in target cells (e.g., stable transformants).

The present methods can include, for example, by administering a recombinant or synthetic Pla2g5 inhibitory nucleic acid into a macrophage produced as described herein. Inhibitory nucleic acids for use in practicing the methods described herein and that are complementary to Pla2g5 can include those which inhibit post-transcriptional processing of Pla2g5 such as inhibitors of mRNA translation (antisense), agents of RNA interference (RNAi), catalytically active RNA molecules (ribozymes), and RNAs that bind proteins and other molecular ligands (aptamers).

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to Pla2g5. Thus, oligonucleotides are chosen that are sufficiently complementary to the target, i.e., that hybridize sufficiently well and with sufficient specificity, to give the desired effect, while striving to avoid significant off-target effects i.e. must not directly bind to, or directly significantly affect expression levels of, transcripts other than the intended target. The optimal length of the antisense oligonucleotide may very but it should be as short as possible while ensuring that its target sequence is unique in the transcriptome i.e. antisense oligonucleotides may be as short as 12-mers (Seth (2009) J Med Chem 52:10-13) to 18-22 nucleotides in length.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridisable. A complementary nucleic acid sequence of the invention is specifically hybridisable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. The antisense oligonucleotides useful in the methods described herein have at least 80% sequence complementarity to a target region within the target nucleic acid, e.g., 90%, 95%, or 100% sequence complementarity to the target region within Pla2g5 (e.g., a target region comprising the seed sequence). Percent complementarity of an antisense compound with a region of a target nucleic acid can be determined routinely using basic local alignment search tools (BLAST programs) (Altschul (1990) J. Mol. Biol. 215, 403-410; Zhang and Madden (1997) Genome Res. 7, 649-656). The specificity of an antisense oligonucleotide can also be determined routinely using BLAST program against the entire genome of a given species For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art. For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York, Hilario (2007) Methods Mol Biol 353:27-38.

Inhibitory nucleic acids for use in the methods described herein can include one or more modifications, e.g., be stabilized against nucleolytic degradation such as by the incorporation of a modification, e.g., a nucleotide modification. For example, inhibitory nucleic acids can include a phosphorothioate at least the first, second, or third internucleotide linkage at the 5' or 3' end of the nucleotide sequence. As another example, inhibitory nucleic acids can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-dimethylaminoethyloxyethyl (2'-O-DMAEOE), or 2'-O—N-methylacetamido (2'-O-NMA). As another example, the inhibitory nucleic acids can include at least one 2'-O-methyl-modified nucleotide, and in some embodiments, all of the nucleotides include a 2'-O-methyl modification.

Modifications

Chemical modifications, particularly the use of locked nucleic acids (LNAs) (Okiba (1997) Tetrahedron Lett 39:5401-5404; Singh (1998) Chem Commun 4:455-456), 2'-O-methoxyethyl (2'-O-MOE) (Martin (1995) Helv Chim Acta 78:486-504; You (2006) Nucleic Acids Res 34(8):e60; Owczarzy (2011) Biochem 50(43):9352-9367), constrained ethyl BNA (cET) (Murray (2012) Nucleic Acids Res 40: 6135-6143), and gapmer oligonucleotides, which contain 2-5 chemically modified nucleotides (LNA, 2'-O-MOE RNA or cET) at each terminus flanking a central 5-10 base "gap" of DNA (Monia (1993) J Biol Chem 268:14514-14522; Wahlestedt (2000) PNAS 97:5633-5638), improve antisense oligonucleotide binding affinity for the target RNA, which increases the steric block efficiency. Antisense and other compounds that hybridize to Pla2g5 are identified through experimentation, and representative sequences of these compounds are herein below identified as preferred embodiments of the invention (e.g., including but not limited to the antisense oligonucleotide or siRNAs of SEQ ID NO. 5 (AGAGAAACCUACGGAGCUA), SEQ ID NO. 6 (AGAACGCCCUGACAAACUA) SEQ ID NO. 7 (GAGAAGGGCUGCAACAUUC), or SEQ ID NO. 8 (GCACACAGUCCUACAAAUA).

Techniques for the manipulation of inhibitory nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. In some embodiments, the inhibitory nucleic acids are "locked," i.e., comprise nucleic acid analogues in which the ribose ring is "locked" by a methylene bridge connecting the 2'-O atom and the 4'-C atom (see, e.g., Kaupinnen (2005) Drug Disc. Today 2(3): 287-290; Koshkin (1998) J. Am. Chem. Soc. 120(50): 13252-13253). For additional modifications see US 20100004320, US 20090298916, and US 20090143326.

The LNA molecules can be designed using any method known in the art; a number of algorithms are known, and are commercially available (e.g., exiqon.com). You (2006) Nuc. Acids. Res. 34:e60; McTigue (2004) Biochemistry 43:5388-405; and Levin (2006) Nuc. Acids. Res. 34:e142. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the nucleic acid. For example, a specific functional region can be targeted, e.g., a region comprising a known RNA localization motif (i.e., a region complementary to the target nucleic acid on which the nucleic acid acts), or a region comprising a known protein binding region, e.g., a Polycomb (e.g., Polycomb Repressive Complex 2 (PRC2), comprised of H3K27 methylase EZH2, SUZ12, and EED)) or LSD1/CoREST/REST complex binding region (Tsai (2010) Science 329(5992): 689-93; and Zhao (2008) Science 322(5902):750-6; Sarma (2010) PNAS 107 (51): 22196-201). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul (1990) J. Mol. Biol. 215, 403-410; Zhang and Madden (1997) Genome Res. 7, 649-656), e.g., using the default parameters.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin (1998) Tetrahedron 54, 3607-3630; Obika (1998) Tetrahedron Lett. 39, 5401-5404; Jepsen (2004) Oligonucleotides 14:130-146; Kauppinen (2005) Drug Disc. Today 2(3):287-290; and Ponting (2009) Cell 136(4):629-641, and references cited therein.

See also U.S. Ser. No. 61/412,862, which is incorporated by reference herein in its entirety.

siRNA/shRNA

In some embodiments, the nucleic acid sequence that is complementary to Pla2g5 can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference. RNA interference may cause translational repression and degradation of target mRNAs with imperfect complementarity or sequence-specific cleavage of perfectly complementary mRNAs.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the Rnase III family. The siRNA is then capable of inhibiting the expression of a gene with which it shares homology. After the siRNA has cleaved its target, it is released from that RNA to search for another target and can repeatedly bind and cleave new targets (Brummelkamp (2002) Science 296:550-553; Lee (2002) Nature Biotechnol., 20, 500-505; Miyagishi and Taira (2002) Nature Biotechnol 20:497-500;

Paddison (2002) Genes & Dev. 16:948-958; Paul (2002) Nature Biotechnol 20, 505-508; Sui (2002) Proc. Natl. Acad. Sd. USA 99(6), 5515-5520; Yu (2002) Proc Natl Acad Sci USA 99:6047-6052; Peer and Lieberman (2011) Gen Ther 18, 1127-1133).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus, the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target. shRNAs that are constitutively expressed form promoters can ensure long-term gene silencing. Most methods commonly used for delivery of siRNAs rely on commonly used techniques for introducing an exogenous nucleic acid into a cell including calcium phosphate or calcium chloride precipitation, microinjection, DEAE-dextrin-mediated transfection, lipofection, commercially available cationic polymers and lipids and cell-penetrating peptides, electroporation or stable nucleic acid-lipid particles (SNALPs), all of which are routine in the art. siRNAs can also be conjugated to small molecules to direct binding to cell-surface receptors, such as cholesterol (Wolfrum (2007) Nat Biotechnol 25:1149-1157), alpha-tocopherol (Nishina (2008) Mol Ther 16:734-40), lithocholic acid or lauric acid (Lorenz (2004) Bioorg Med Chem Lett 14:4975-4977), polyconjugates (Rozema (2007) PNAS 104:12982-12987). A variation of conjugated siRNAs are aptamer-siRNA chimeras (McNamara (2006) Nat Biotechnol 24:1005-1015; Dassie (2009) Nat Biotechnol 27:839-849) and siRNA-fusion protein complexes, which is composed of a targeting peptide, such as an antibody fragment that recognizes a cell-surface receptor or ligand, linked to an RNA-binding peptide that can be complexed to siRNAs for targeted systemic siRNA delivery (Yao (2011) Sci Transl Med 4(130):130ra48.

Ribozymes

Trans-cleaving enzymatic nucleic acid molecules can also be used; they have shown promise as therapeutic agents for human disease (Usman & McSwiggen, (1995) Ann. Rep. Med. Chem. 30, 285-294; Christoffersen and Marr (1995) J. Med. Chem. 38, 2023-2037; Weng (2005) Mol Cancer Ther 4, 948-955; Armado (2004) Hum Gene Ther 15, 251-262; Macpherson (2005) J Gene Med 7, 552-564; Muhlbacher (2010) Curr Opin Pharamacol 10(5):551-6). Enzymatic nucleic acid molecules can be designed to cleave specific Pla2g5 targets within the background of cellular RNA. Such a cleavage event renders the Pla2g5 mRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel (1979) Proc. R. Soc. London B 205, 435) have been used to evolve new nucleic acid catalysts with improved properties, new functions and capable of catalyzing a variety of reactions, such as cleavage and ligation of phosphodiester linkages and amide linkages, (Joyce (1989) Gene 82, 83-87; Beaudry (1992) Science 257, 635-641; Joyce (1992) Scientific American 267, 90-97; Breaker (1994) TIBTECH 12, 268; Bartel (1993) Science 261:1411-1418; Szostak (1993) TIBS 17, 89-93; Kumar (1995) FASEB J. 9, 1183; Breaker (1996) Curr. Op. Biotech. 1, 442; Scherer (2003) Nat Biotechnol 21, 1457-1465; Berens (2015) Curr. Op. Biotech. 31, 10-15). Ribozymes can also be engineered to be allosterically activated by effector molecules (riboswitches, Liang (2011) Mol Cell 43, 915-926; Wieland (2010) Chem Biol 17, 236-242; U.S. Pat. No. 8,440,810). The development of ribozymes that are optimal for catalytic activity would contribute significantly to any strategy that employs RNA-cleaving ribozymes for the purpose of regulating gene expression. The most common ribozyme therapeutics are derived from either hammerhead or hairpin/paperclip motifs. The hammerhead ribozyme, for example, functions with a catalytic rate (kcat) of about 1 min-1 in the presence of saturating (10 rnM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Ribozymes can be delivered to target cells in RNA form or can be transcribed from vectors. Due to poor stability of fully-RNA ribozymes, ribozymes often require chemical modification, such as, 5'-PS backbone linkage, 2'-O-Me, 2'-deoxy-2'-C-allyl uridine, and terminal inverted 3'-3' deoxyabasic nucleotides (Kobayashi (2005) Cancer Chemother Pharmacol 56, 329-336).

Antagomirs

In some embodiments, the antisense is an antagomir. Antagomirs are chemically modified antisense oligonucleotides that target a nucleic acid or miRNA (U.S. Pat. No. 8,937,217). For example, an antagomir for use in the methods described herein can include a nucleotide sequence sufficiently complementary to hybridize to a Pla2g5 target sequence of about 12 to 25 nucleotides, preferably about 15 to 23 nucleotides.

In general, antagomirs include a cholesterol moiety, e.g., at the 3'-end. In some embodiments, antagomirs have various modifications for Rnase protection and pharmacologic properties such as enhanced tissue and cellular uptake. For example, In addition to the modifications discussed above for antisense oligonucleotides, an antagomir can have one or more of complete or partial 2'-O-methylation of sugar and/or a phosphorothioate backbone. Phosphorothioate modifications provide protection against Rnase activity and their lipophilicity contributes to enhanced tissue uptake. In some embodiments, the antagomir cam include six phosphorothioate backbone modifications; two phosphorothioates are located at the 5'-end and four at the 3'-end. See, e.g., Krutzfeldt (2005) Nature 438, 685-689; Czech (2006) N Engl J Med, 354:1194-1195; Robertson (2010) Silence.

1:10; Marquez and McCaffrey (2008) Hum Gene Ther., 19(1):27-38; van Rooij (2008) Circ Res. 103(9):919-928; and Liu (2008) Int. J. Mol. Sci. 9:978-999; (Ebert (2010) RNA 16, 2043-2050). Antagomirs useful in the present methods can also be modified with respect to their length or otherwise the number of nucleotides making up the antagomir. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir; Krutzfeldt (2005) Nature 438, 685-689).

In some embodiments, the antisense is a miRNA sponge or a variation of miRNA sponge, such as target mimics (Franco-Zorrilla (2007) Nat Genet 39:1033-1037), decoys (Care (2007) Nat Med 13:613-618, miRNA target sequences (Gentner (2009) Nat Methods 6:63-66), miRNA erasers (Sayed (2008) Mol Biol Cell 19:3272-3282), and lentivirus-mediated antagomirs (Scherr (2007) Nucleic Acid Res 35:e149). Sponge constructs typically contain 4-10 binding sites separated by a few nucleotides each. The efficacy of miRNA sponges depends on affinity and avidity of binding sites, as well as the concentration of sponge RNAs relative to the concentration of the miRNA.

CRISPR Pla2g5 Gene Editing Complexes

The present methods include the use of CRISPR Pla2g5 gene editing complexes. The methods can include the use of expression vectors for transfection and expression of a Cas9 protein and suitable guide RNAs targeting Pla2g5. Alternatively, or in addition, the methods can include the use of purified Cas9 proteins complexed with suitable guide RNAs targeting Pla2g5.

Nucleic Acids Encoding a CRISPR Pla2g5 Gene Editing Complex

The present methods include the delivery of nucleic acids encoding a CRISPR Pla2g5 gene editing complex. The gene editing complex includes a Cas9 editing enzyme and one or more guide RNAs directing the editing enzyme to Pla2g5.

Guide RNAs Directing the Editing Enzyme to Pla2g5

The gene editing complex also includes guide RNAs directing the editing enzyme to Pla2g5, i.e., comprising a sequence that is complementary to the sequence of a nucleic acid encoding Pla2g5, and that include a PAM sequence that is targetable by the co-administered Cas9 editing enzyme. In some embodiments, the precursor sequence is targeted by the guide RNA., i.e., comprising a sequence that is complementary to the sequence of a nucleic acid encoding Pla2g5. In some embodiments, the precursor sequence is targeted by the guide RNA.

The gene encoding the human Pla2g5 precursor is at nucleotides 20028350-20091901 of chromosome 11, Reference GRCh38.p7 Primary Assembly (see GenBank Acc. No. NG_032045.1).

Other Cas9s from other species can also be used, including those shown in Table 1. Suitable target sequences for use with those Cas9s can readily be determined using known methods.

TABLE 1

Exemplary Cas9s

| Species/Variant of Cas9 | PAM Sequence |
| --- | --- |
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| Streptococcus thermophilus (ST) | NNAGAAW |
| Treponema denticola (TD) | NAAAAC |
| Streptococcus pyogenes (SP); SpCas9 | NGG |
| Staphylococcus aureus (SA); SaCas9 | NNGRRT or NNGRR(N) |
| Neisseria haracteriza (NM) | NNNNGATT |

Cas9 Editing Enzymes

The methods include the delivery of Cas9 editing enzymes to the cells. The editing enzymes can include one or more of SpCas9 D1135E variant; SpCas9 VRER variant; SpCas9 EQR variant; SpCas9 VQR variant; Streptococcus thermophilus (ST) Cas9 (StCas9); Treponema denticola (TD) (TdCas9); Streptococcus pyogenes (SP) (SpCas9); Staphylococcus aureus (SA) Cas9 (SaCas9); or Neisseria haracteriza (NM) Cas9 (NmCas9), as well as variants thereof that are at least 80%, 85%, 90%, 95%, 99% or 100% identical thereto that retain at least one function of the parent case, e.g., the ability to complex with a gRNA, bind to target DNA specified by the gRNA, and alter the sequence of the target DNA.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

The PAM sequences of these Cas9s are listed in Table 1, above. The sequences of the Cas9s are known in the art; see, e.g., Kleinstiver et al., Nature. 2015 Jul. 23; 523(7561): 481-485; WO 2016/141224; U.S. Pat. No. 9,512,446; US-2014-0295557; WO 2014/204578; and WO 2014/144761. The methods can also include the use of the other previously described variants of the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), FokI-dCas9 fusions (Guilinger et al., Nat Biotechnol 32, 577-582 (2014); Tsai et al., Nat Biotechnol 32, 569-576 (2014); WO2014144288).

The SpCas9 wild type sequence is as follows:

(SEQ ID NO: 9)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

The SaCas9 wild type sequence is as follows:

(SEQ ID NO: 10)
MKRNYILGLDIGITSVGYGIIDYETRDVIDAGVRLFKEANVENNEGRRSK

RGARRLKRRRRHRIQRVKKLLFDYNLLTDHSELSGINPYEARVKGLSQKL

SEEEFSAALLHLAKRRGVHNVNEVEEDTGNELSTKEQISRNSKALEEKYV

AELQLERLKKDGEVRGSINRFKTSDYVKEAKQLLKVQKAYHQLDQSFIDT

YIDLLETRRTYYEGPGEGSPFGWKDIKEWYEMLMGHCTYFPEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEENSKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG

See also Hou, Z. et al. Efficient genome engineering in human pluripotent stem cells using Cas9 from *Neisseria haracteriza*. Proc Natl Acad Sci USA (2013); Fonfara, I. et al. Phylogeny of Cas9 determines functional exchangeability of dual-RNA and Cas9 among orthologous type II CRISPR-Cas systems. Nucleic Acids Res 42, 2577-2590 (2014); Esvelt, K. M. et al. Orthogonal Cas9 proteins for RNA-guided gene regulation and editing. Nat Methods 10, 1116-1121 (2013); Cong, L. et al. Multiplex genome engineering using CRISPR/Cas systems. Science 339, 819-823 (2013); Horvath, P et al. Diversity, activity, and evolution of CRISPR loci in *Streptococcus thermophilus*. J Bacteriol 190, 1401-1412 (2008).

As noted above, the Cas9 can be delivered as a purified protein (e.g., a recombinantly produced purified protein, prefolded and optionally complexed with the sgRNA) or as a nucleic acid encoding the Cas9, e.g., an expression construct. Purified Cas9 proteins can be produced using methods known in the art, e.g., expressed in prokaryotic or eukaryotic cells and purified using standard methodology. See, e.g., Liang et al., Journal of Biotechnology 208:44-53 (2015); Kim et al., Genome Res. 2014 June; 24(6): 1012-1019. Efficiency of protein delivery can be enhanced, e.g., using electroporation (see, e.g., Wang et al., Journal of Genetics and Genomics 43(5):319-327 (2016)); cationic or lipophilic carriers (see, e.g., Yu et al., Biotechnol Lett. 2016; 38: 919-929; Zuris et al., Nat Biotechnol. 33(1):73-80 (2015)); or even lentiviral packaging particles (see, e.g., Choi et al., Gene Therapy 23, 627-633 (2016)).

CRISPR Expression Constructs

Expression constructs encoding one or both of guide RNAs and/or Cas9 editing enzymes can be administered in any effective carrier, e.g., any formulation or composition capable of effectively delivering the component gene to cells. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, haracteri S, artificial viral envelopes or other such intracellular carriers, as well as direct injection of the gene construct or CaPO$_4$ precipitation.

A preferred approach for introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes. These vectors provide efficient delivery of genes into cells, and the transferred nucleic acids are stably integrated into the chromosomal DNA of the host cell. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

As demonstrated herein, a lentiviral CRISPR-Cas9 targeting system provided high and tumor-specific expression of Cas9, the corresponding high Pla2g5 editing efficacy in tumor tissues, while lacking general toxicity or neurotoxicity. Lentiviral vectors transduce dividing as well as quiescent cells. This can be viewed as a major advantage with respect to gene therapy for tumors in general, as within a short treatment window most tumor cells (and especially GSC) do not divide. Therapeutic use of the lentiviral editing approach can be a legitimate alternative to other viral systems, as high viral titers can be produced, nonproliferating cells that are especially abundant in the walls of the tumor cavity after surgery can be transduced, and transduction efficacies are very high. An additional advantage of a locally applied vesicular stomatitis virus glycoprotein (VSV-G) pseudo-typed lentivirus is its inactivation by human serum that would reduce systemic effects. To further reduce neurotrophism, and enhance selective tropism for glioma and GSC, the commonly bound envelope glycoprotein of VSV can be replaced with a more selective variant glycoprotein of lymphocytic choriomeningitis virus (LCMV-GP). LCMV-GP is not cytotoxic when injected locally or systemically, can be packaged with other components of the CRISPR-Cas9 system, and efficiently transduces solid glioma tissues as well as infiltrating tumor cells.

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Pla2g5 genome-editing vectors based on recombinant Adenovirus-5 (Ad5): Ad5 have many advantages for this purpose, including non-integration, lack of insertional mutagenesis, high-efficiency transduction, and accommodation of large expression cassettes; these vectors have also been utilized in multiple clinical trials.

Helper-dependent (HDAd) vectors can also be produced with all adenoviral sequences deleted except the origin of DNA replication at each end of the viral DNA along with packaging signal at 5-prime end of the genome downstream of the left packaging signal. HDAd vectors are constructed and propagated in the presence of a replication-competent helper adenovirus that provides the required early and late proteins necessary for replication.

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. And Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993). The identification of Staphylococcus aureus (SaCas9) and other smaller Cas9 enzymes that can be packaged into adeno-associated viral (AAV) vectors that are highly stable and effective, easily produced, approved by FDA, and tested in multiple clinical trials, paves new avenues for therapeutic gene editing. Of high relevance to GBM, better tissue distribution of AAV provides an additional advantage for invasive and recurrent tumors. Pla2g5-targeting AAV vectors of various serotypes, including AAV1, AAV2, AAV8, AAV9, and AAVrh.10, can be used, all of which were previously tested in clinical trials. Pla2g5 targeting AAV plasmid [based on Addgene Plasmids #61592, #61594], a single vector expressing SaCas9, gRNA, and Ampicillin selection marker can be utilized. Since PAM consensus sequence is different between SpCas9 and SaCas9 (the late cleaves genomic targets most efficiently with NNGRRT or NNGRR (R=A or G), as also the length required for SaCas9 gRNAs (21-23 nt), several targeting constructs have been designed.

Preferably, the CRISPR Pla2g5 editing complex is specific, i.e., induces genomic alterations preferentially at the target site (Pla2g5), and does not induce alterations at other sites, or only rarely induces alterations at other sites.

Administration

The present methods include delivery of the autologous Pla2g5-deficient suppressive macrophages into the airways of a subject. This can be achieved, e.g., using an aerosol spray of a suspension of cells into the nasal passage, or intratracheal (Urbanek et al., PloS One. 2016; 11(7): e0158746) or intrabracheal distilliation of a suspension of cells, e.g., via bronchoscopy (see Morales et al., BMC Pulmonary Medicine201515:66), or by intravenous delivery of the cells (since cells delivered IV pass through and may be entrapped therein, see Kean et al., Stem Cells International, Volume 2013 (2013), Article ID 732742, 13 pages). Preferably, the cells will be suspended in a physiologically acceptable media or buffer. In some embodiments, the cells are administered every 5 days, 7 days, every 10 days, e.g., when used as therapy for severe asthmatics, or every 2-3 weeks, or once a month. In some embodiments, the methods include administering 2, 3, of the 4 doses of the Pla2g5-deficient suppressive macrophages, and then no additional doses, or further doses as needed for flare-ups.

The cell compositions can be provided in a container, pack, or dispenser together with instructions for administration.

EXAMPLES

The invention is further described in the following examples, which do not limit the scope of the invention described in the claims.

Methods

The following materials and methods were used in the Examples below.

Lung Inflammation

C57/BL6 Wt and Pla2g5-null mice[46, 47] (9-12 wk-old males) received 25 µg of *Alternaria haracter* extract (Greer Laboratories, Lenoir, N.C.) in 20 uL of PBS or PBS alone intranasally on days 0, 3, 6 and 9 and euthanized 18 hours later[1] or a single dose of 100 µg and were euthanized after 1 h or 3 h[2]. For IL-33-induced pulmonary inflammation, Wt and Pla2g5-null naïve mice were given mouse rIL-33 (R&D Systems, Minneapolis, Minn.) intranasally (i.n.) 100 ng/dose on days 0, 3, 6 and 9 with or without LA (132 nM)[28] or OA (106 nM), and mice were euthanized 18 hours after the last dose.

All animal experiments were approved by the Animal Care and Use Committee of the Dana-Farber Cancer Institute (Boston, Mass.).

Flow Cytometry

Lung were manually chopped to approximately 10 mm pieces, then digested in RPMI containing 428 U/ml Collagenase IV (Worthington, Lakewood, N.J.) and 20 mg/ml DNAse I (Roche, Mannheim, Germany) (30 min, 37° C.). After red cell lysis, the obtained cell suspension from single mouse was washed, and counted. After washing, cells were blocked (1 h, 4° C.) with 1% of rat anti mouse CD16/CD32 (BD Biosciences, San Jose, Calif.) and 10% donkey serum and then stained (1 h, 4° C.) with appropriate Abs. Mouse cells were stained with CD45 PercPCy5 (clone 30-F11, BioLegend, San Diego, Calif.), CD19 FITC (6D5, Biolegend), CD3 FITC (145-2C11, BioLegend), CD11b FITC (M1/70, BioLegend), CD11c PE-Cy7 FITC (N418, BioLegend), Ly6G/C FITC (RB6-8C5, eBiosciences), Nk1.1 FITC (PK136, Biolegend), FceR1 FITC (MAR-1, Biolegend), Siglec-F APC (E50-2440, BD Bioscience), Thy 1.2 APC (53-2.1, eBioscience, San Diego, Ca), ICOS (C398.4A, eBiosciences), Sca-1 (D7, eBioscieces), CD25 (PC61, eBiosciences), ST2 biotin (clone DJ8, MD Bioscience) followed by PE streptavidin (eBiosciences). In selected experiments cells were fixed with 4% paraformaldehyde (7 min, 21° C.), washed, permeabilized with 0.1% saponin (SigmaAldrich, St Louis, Ca) (7 min, 21° C.) and stained with CD68 APC (FA-11, AbD Serotec, Raleigh, Nc), IL-5 PE (TRFKS, Biolegend), IL-13 (eBio13A eBiosciences), IL-33 PE (396118, R&D Systems, Minneapolis, Minn.), rabbit polyclonal anti murine RELM-a (Peprotech, Rocky Hill N.J.)) and corresponding isotypes as controls. Acquisition was performed on a FACSCanto flow cytometer with FACSDiva software (BD Biosciences), and data were analyzed with FlowJo (Tree Star, Ashland, Oreg.).

Airways Analysis and Lung Cell Processing

Bronchoalveolar lavage (BAL) was performed with 0.7 mL PBS (Sigma-Aldrich) containing 0.5 mM EDTA (three times). The BAL fluid was collected, and cell-free supernatant was aliquoted and frozen. ELISA was used to measure IL-33 (R&D Systems).

Western Blot

Right lungs were collected at time of euthanasia and snap frozen. Proteins were isolated from tissue homogenates in RIPA buffer (Boston Bioproducts, Ashland, Mass., USA) with protease inhibitors[26]. The protein concentration in cell lysates was measured using the BCA Assay (Pierce, Thermo Scientific) and 20 µg of proteins were separated on a 10-20% Tris-Glycine gel (Novex, Life Technologies) and then transferred to a PVDF membrane. After blocking overnight at 4° C. in 5% milk, the blots were incubated with a goat polyclonal IL-33 (1:500, R&D Systems) or mouse monoclonal β-actin (1:1000, Cell Signaling, Danvers, Mass.) antibodies diluted in TBST at RT for 2h, followed by a rabbit anti-goat or goat anti-mouse secondary antibody (1:3000, BioRad) diluted in TBST for 1 hour at RT. The blots were visualized using the Supersignal West Femto Chemiluminescent substrate (Thermo Scientific) and imaged by a KODAK M35A X-OMAT processor.

Frozen Sections

Lungs of Wt and Pla2g5-null mice were excised and immersed in RPMI. Within 1h of surgery, the tissue was removed from RPMI and fixed in 4% paraformaldehyde, then embedded in Tissue-Tek® O.C.T.™ Compound (Sakura Finetek), and kept at −80° C. until sectioning. Sections of 5-μm thickness were freshly cut, thaw-mounted onto slides, and stained for confocal microscopy. Frozen sections were rehydrated for 1 hour at RT then blocked with 10% donkey serum, followed by incubation with goat polyclonal IL-33 (AF3626, R&D Systems) and rabbit polyclonal proSPC (AB3786, Millipore, Temecula, Calif.) antibodies or appropriate isotypes controls at 4° C., overnight. Samples were washed and incubated at RT for 1 hour with appropriate secondary antibodies. The sections were washed and covered with Fluoroshield mounting media (Electron Microscopy Sciences, Hatfield, Pa.). Sections were imaged using a Nikon C1 plus laser scanner confocal system with a 40× oil Plan-Fluor NA1.3 objective lens. 8-10 Z-stack images of 0.5 μm were acquired through a small pinhole using Nikon EZ-C1 software. Images were analyzed using Image J (U.S. National Institute of Health, Bethesda, Md.).

BM Macrophage Transfer

Wt bone marrow (BM) cells were collected from femurs and tibiae of mice. The disaggregated cells were counted and suspended in complete medium (DMEM F12, 5% FBS, 100U/ml penicillin, 100 ug/ml streptomycin, 0.1 mM non-essential amino acids, 2 mM L-glutamine and 0.05 μM 2-ME) containing 50 ng/ml murine r-MCSF (PeproTech) at a concentration of $4.0 \times 10^6$ cells/ml in a 10 ml/Petri dish. On day 3, 10 ml of medium containing r-MCSF were added to each dish. On day 7, cells were harvested with PBS containing Lidocaine (4 mg/ml, 15 min, 37 C) and resuspended at concentration of $5 \times 10^6$ cells/ml in PBS. For adoptive transfer, $1 \times 10^5$ BM-macrophages were transferred i.t. into Wt and Pla2g5-null mice two days after the first dose of *Alternaria* followed by 3 more doses of *Alternaria* (25 μg in 20 μl PBS) intranasally (i.n.) on day 3, 6 and 9. Mice were euthanized 18h after last dose.

Mass Spectrometry of Lipids

Wt and Pla2g5-null BM-macrophages were cultured for 7 days in r-MCSF. Adherent cells were collected, frozen and shipped for analysis by mass spectrometry. Free fatty acid analysis was performed according to a previously published method[32, 48]. Briefly, the cell pellet was homogenized in 500 ul of PBS/10% methanol. An aliquot of 200 μl corresponding to about $0.5 \times 10^6$ cells was withdrawn and a cocktail of internal standards consisting of 15 deuterated fatty acids was added. The extraction was initiated with 500 μl of methanol and 25 μl of 1N HCl and a bi-phasic solution is formed by addition of 1.5 ml of isooctane. The phases are separated by centrifugation and the isooctane phase containing the free fatty acids FFA fraction was removed. The extraction is repeated once and the combined extracts are evaporated to dryness. The free fatty acids were derivatized with pentafluorobenzyl (PFB) bromide and the resulting fatty acid PFB esters were analyzed by gas chromatography/mass spectrometry using a negative chemical ionization mode (Agilent 6890N gas chromatograph equipped with an Agilent 5973 mass selective detector; Agilent, Santa Clara, Calif.). Standard curves for each of the fatty acids were acquired in parallel using identical conditions. The quantitative assessment of fatty acids in a sample was achieved by comparison of the mass spectrometric ion signal of the target molecule normalized to the internal standard with the matching standard curve according to the isotope dilution method and by protein content[32].

ILC2 Cells Sorting and Culture

Wt and Pla2g5-null mice received four doses of 25 ug of *Alternaria* in 20 ul of PBS intranasally on day 0, 3, 6 and 9 and euthanized 18h later in order to expand ILC2 prior to FACs sorting. Sorting of ILC2 (CD45+ Lin− (CD3, CD19, Ly6g, CD11c, CD11b, Nk1.1, FcεR1−), Thy1.2+) was performed using a FACSDiva 8.0.1 cell sorter (BD bio-science). Purified ILC2 (>98%) were rested for 40 hours with 10 ng/mL rIL-2 and rIL-7 (R&D Systems, Minneapolis, Minn.) in a 96 well around bottom plates (20000 cells per well). Prior to stimulation, the medium was changed to fresh medium. ILC2 were cultured with 30 ng/mL rIL-33 (R&D Systems), 200 μM Linoleic Acid (Cayman Chemical) or 200 μM Oleic Acid (Cayman Chemical)[22] or all together for 8h. For intracellular cytokine staining, 1 μl/mL of Golgi Plug (BD Bioscience) was added to ILC2 6h before collection for FACs analysis.

Real-Time PCR

Total RNA was isolated from lysate with the Rneasy Micro Kit (Qiagen, Louisville, Ky., USA), reverse transcribed into cDNA (High-Capacity cDNA Reverse Transcription Kit; Thermo Science-Applied Biosystems, Foster City, Calif., USA) and measured by real-time PCR for FFAR1 and Pla2g5 with the use of SYBR Green/ROX master mix (SABiosciences, Frederick, Md., USA) on an Mx3005P thermal cycler (Stratagene, Santa Clara, Calif., USA). The ratio of each mRNA relative to the GAPDH mRNA was calculated with the $^{\Delta\Delta}Ct$ threshold cycle method. The mouse primers used were GAPDH F: TCAACAGCAACTCCCACTCTTCCA (SEQ ID NO:1); R: ACCCTGTTGCTGTAGCCGTATTCA (SEQ ID NO:2). Pla2g5 F: TGGTTCCTGGCTTGCAGTGTG (SEQ ID NO:3); R: TTCGCAGATGACTAGGCCATT (SEQ ID NO:4). FFAR1/GPR40 and FFAR4/GPR120 were from Qiagen.

Real-time PCR products were run on a 1.5% agarose gel and visualized using chemImager 4400 fluorscience system (Alpha Innotech, Missouri, TEX, USA).

Human Monocyte-Derived Mφ

Leukocyte-enriched buffy coat from healthy donors was overlaid on Ficoll-Paque Plus (GE Healthcare, Buckinghamshire, UK) and centrifuged at 600 g for 20 min. The mononuclear layer at the interface was collected, washed, and counted. Monocytes were isolated by negative selection (Miltenyi Biotec, Auburn, Calif.) and plated at $1-1.5 \times 10^6$ cells/ml in 30-mm Petri dishes, or $2.2 \times 105$ cells/cm2 in 100-mm Petri dishes (Ohta et al., J Immunol 190, 5927-5938). To derive macrophages, monocytes were cultured for 13 days in complete medium (RPMI 1640, 10% FBS, 2 mM L-glutamine, 100U/ml penicillin, 100 μg/ml streptavidin, 10% non-essential amino acids, 1% HEPES, 1% sodium pyruvate, 50 μM 2-ME) supplemented with 50 ng/ml human rGM-CSF (R&D Systems, Minneapolis, Minn.) (Martinez et al. Blood 121, e57-69; Beyer et al., PloS One 7, e45466). To activate macrophages, cells were polarized for 6, 18, 24, or 48 hours in complete medium, supplemented with 40 ng/ml human IL-4 (R&D Systems). To knock down PLA2G5, after culturing the monocytes for 13 days in recombinant GM-CSF, cells were transfected with human PLA2G5 ON-TARGET Plus SMART Pool siRNA or non-targeting vector ON-TARGET Plus Control Pool (1000 nM; GE Dharmacon, Lafayette, Colo.) using the Amaxa Human Macrophage Nucleofector kit (Amaxa, Lonza, Germany), according to the manufacturer's instructions. After 24 h, the transfection medium was replaced by complete medium. Twenty-four hours later, cells were polarized with IL-4 for 6, 18, 24 or 48h. In selected experiments PGE2 or human recombinant PLA2G5 (Cayman, Ann Arbor, Mich.) was added to cells (Ishitanit et al., J Biochem 104, 397-402).

Statistical Analysis

Comparisons between 2 groups were made by using unpaired Student's t test. To compare three or more groups, we performed One-way ANOVA with Sidak's correction for multiple comparisons. Comparisons were performed with Prism software (GraphPad, La Jolla, Calif.). Data are expressed as mean±SEM, and P<0.05 was considered significant.

Example 1. Pulmonary Inflammatory Response to *Alternaria* Requires Pla2g5

To investigate the role of Pla2g5 in activation of ILC2, we used a model of allergic pulmonary inflammation induced by *Alternaria*, which relies on ILC2 activation to cause eosinophilic inflammation. We administered *Alternaria* (25 µg/dose) every two days for four doses and lungs were collected 18h after the last dose[1]. Wt mice treated with *Alternaria* had significantly increased total lung cell numbers compared to *Alternaria*-treated Pla2g5-null mice (FIG. 1A). The number of eosinophils (identified as CD45+/CD11c−/SiglecF+ cells)[29] in *Alternaria*-treated Wt lungs was significantly higher than in *Alternaria*-treated Pla2g5-null lungs (FIG. 1B). *Alternaria*-treated Wt mice had a significantly higher number of ILC2s, identified as CD45+, Lin−, Thy1.2+ cells[9], than equivalently treated Pla2g5-null mice (FIG. 1C), although the percentages were similar (FIG. 1C and data not shown). The numbers (FIG. 1D) and percentages of lung ILC2 expressing the activation markers Sca-1, ST2, CD25, ICOS were drastically reduced in *Alternaria*-treated Pla2g5-null mice compared to ILC2 isolated from equally treated Wt mice. The numbers of ILC2s expressing IL-5 or IL-13 were also significantly reduced in Pla2g5-null mice treated with *Alternaria* compared to Wt mice (FIG. 1E).

Example 2. Induced IL-33 Generation Requires Pla2g5

Figure 2B:
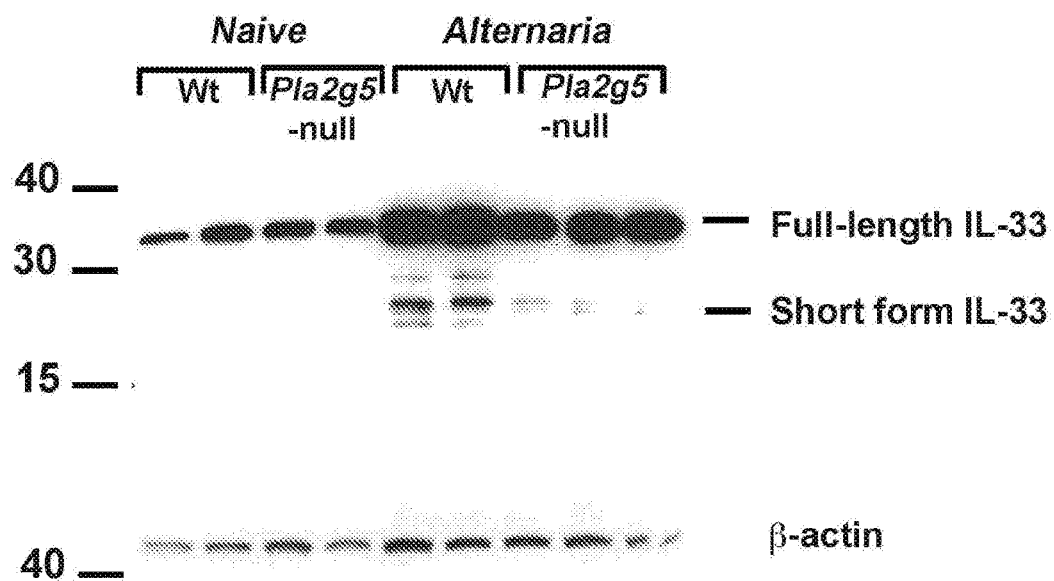

Whereas IL-33 is constitutively expressed by lung barrier cells, its expression can also be upregulated during sustained inflammatory responses, in part reflecting the contributions from hematopoietic cells[30]. To investigate whether the reduced ILC2 activation in Pla2g5-null mice was due to lack of either constitutive or inducible pools of IL-33, we measured IL-33 release into the BAL fluids of I mice after administration of a single *Alternaria* dose. We also monitored the content of IL-33 in the lung at baseline and after 4 doses of *Alternaria* using western blotting. We found that I Wt and Pla2g5-null mice released similar amounts of IL-33 into BAL at 1 and 3 hours after *Alternaria* challenge (FIG. 2A), and showed equivalent amounts of immunoreactive IL-33 in lung lysates (FIG. 2B). Only the full-length IL-33 was detected in the I mice. After ten days and four doses of *Alternaria*, Wt lungs had increased amounts of IL-33 protein compared to naïve mice, and both the preformed full-length form (34 kDa) and the proteolytically processed short length form (18 kDa) were present. Compared with the *Alternaria*-treated Wt controls, the lungs of Pla2g5-null mice showed sharply diminished induction of both the 18 and 34 kDa forms of IL-33 (FIG. 2B).

Figure 2C:
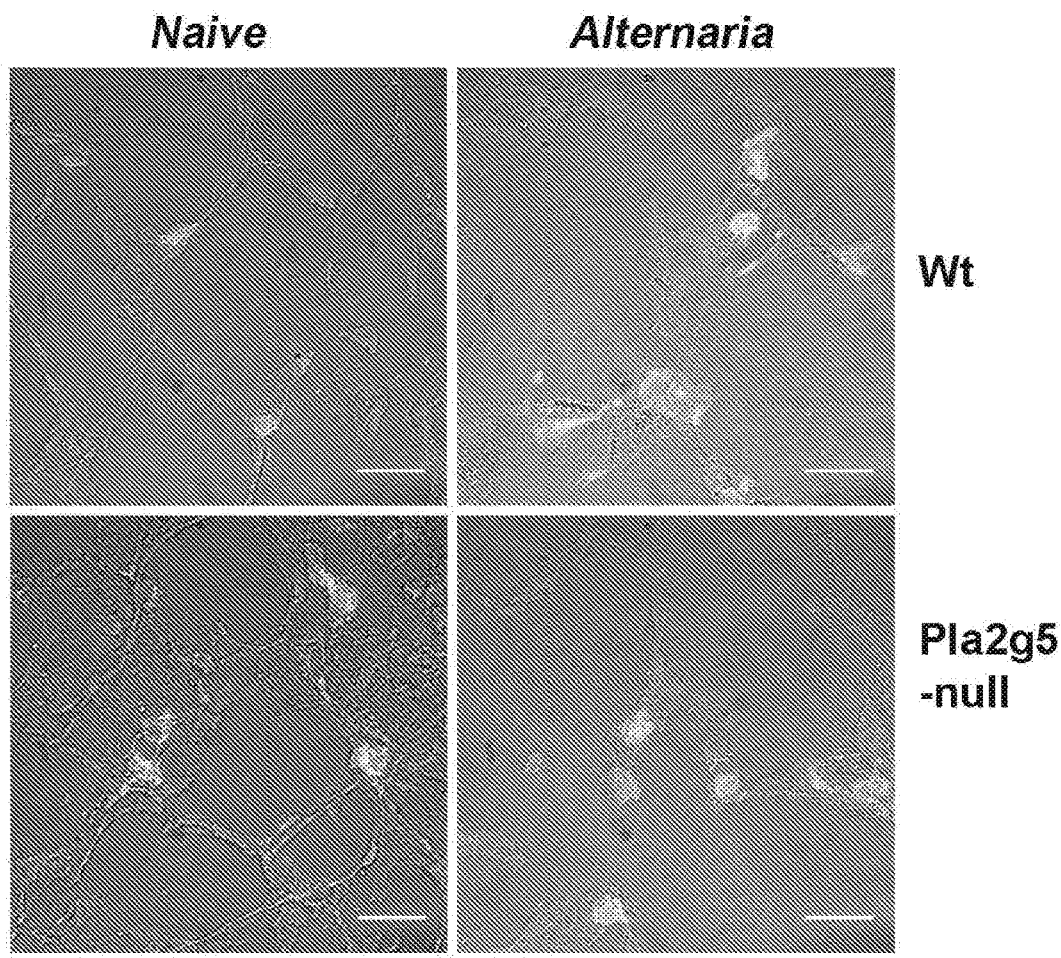
Figure 2D:
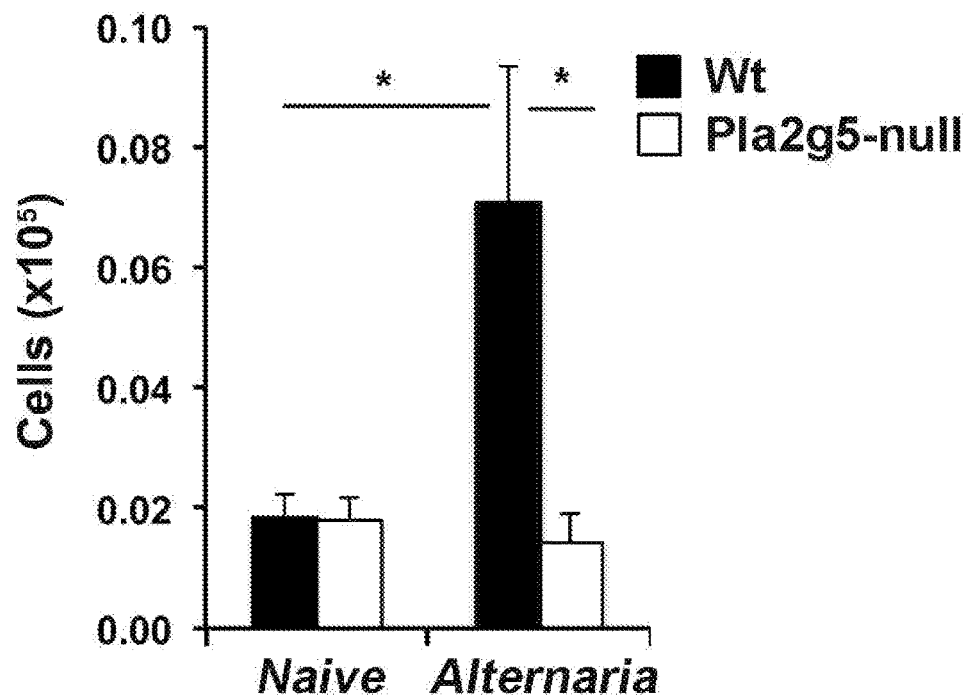
Figure 2E:
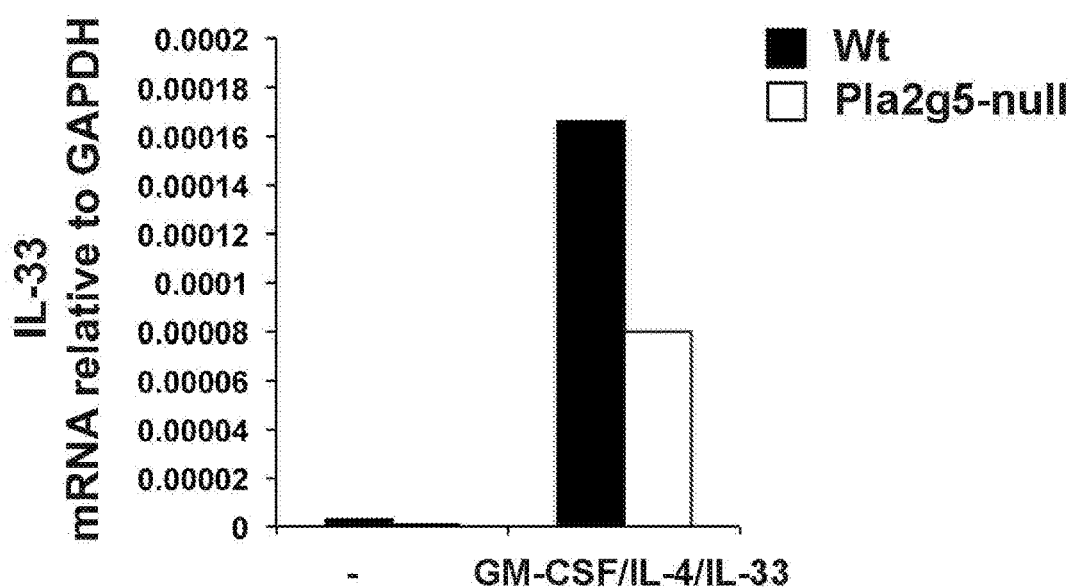

To identify the cellular source(s) responsible for the constitutive and inducible pools of IL-33, we stained frozen sections of Wt and Pla2g5-null mice with anti-IL-33. Since alveolar type 2 pneumocytes (AT2) are one of the major sources of IL-33 in *Alternaria* challenged mice[15], we counterstained the lung sections with Abs against the AT2 cell marker surfactant protein C (SPC). Lungs of both Wt and Pla2g5-null mice showed IL-33 in the nuclei of SPC+AT2 cells at baseline, and there was no difference between Wt and Pla2g5-null *Alternaria* challenged mice (FIG. 2C). Since lung macrophages can also express IL-33 in a model of prolonged exposure to viral allergens[10] and in the recovery phase of IAV infection[31], we used intracellular staining and flow cytometry to determine whether macrophages contributed to the inducible pool of IL-33. Intracellular staining showed that *Alternaria* increased the number of CD68+/IL-33+ macrophages in Wt mice (FIG. 2D). The number of CD68+/IL-33+ cells was significantly reduced in *Alternaria*-treated Pla2g5-null mice. To determine whether cell-intrinsic Pla2g5 was involved in inducing IL-33 expression by macrophages, we stimulated Wt and Pla2g5-null BM-macrophages with GM-CSF, IL-4, and IL-33[25]. Wt BM-macrophages displayed robust induced expression of IL-33 mRNA. In contrast, Pla2g5-null macrophages showed reduced induction (FIG. 2E).

Example 3. Pla2g5-Sufficient Macrophages, but not IL-33 Alone, can Restore ILC2 Activation and Inflammation to Pla2g5-Null Mice Next, we wanted to ascertain whether exogenous recombinant I-IL-33 would restore eosinophilia and ILC2 activation in Pla2g5-null mice. Administration of IL-33 over 10 days (FIG. 3) robustly increased the numbers of eosinophils, ILC2s and Sca-1+ILC2 in Wt mice[3]. Surprisingly, Pla2g5-null mice showed markedly diminished numbers of eosinophils, ILC2 and Sca-1+ILC2 after treatment with IL-33 compared with Wt controls (FIGS. 3A-B). Exogenous IL-33 also induced substantial macrophage activation, as determined by the detection of resistin-like molecule alpha (RELMα) in macrophages, in Wt mice. In contrast, macrophage activation was markedly impaired in IL-33-treated Pla2g5-null animals (FIG. 3B). To determine whether the defect in ILC2 function reflected the effects of cell-intrinsic Pla2g5, we sorted ILC2s from the lungs of Wt mice and performed qPCR. Pla2g5 transcripts were not detected in ILC2s (data not shown).

Figure 4B:
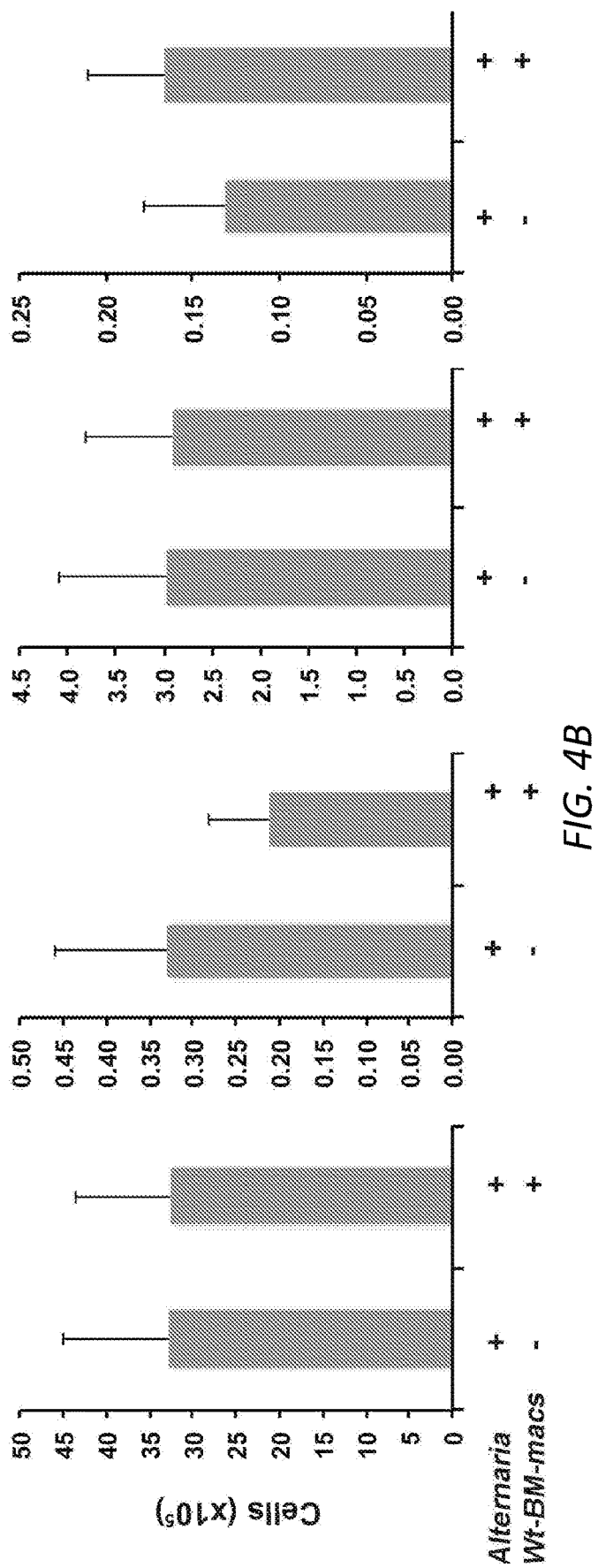

Because macrophages require endogenous Pla2g5 for their functions in pulmonary inflammation[25], we wanted to investigate whether ILC2 activation and downstream lung inflammation could be restored to Pla2g5-null mice by reconstituting Pla2g5 function in macrophages. We adoptively transferred unstimulated Wt BM-macrophages into Wt and Pla2g5-null recipient mice 24h before the second dose of *Alternaria*, then administered 3 more doses and analyzed eosinophils numbers and ILC2 activation (FIGS. 4A-B). Compared to Pla2g5-null mice receiving *Alternaria* without macrophage transfer, Pla2g5-null mice receiving Wt BM-macrophages plus *Alternaria* had significantly higher numbers of eosinophils and significantly higher numbers of ILC2s expressing Sca-1, CD25 or intracellular IL-5 (FIG. 4A). In contrast, the transfer of Wt BM-macrophages into *Alternaria*-treated Wt mice did not significantly increase the recruitment of eosinophils or ILC2 activation compared to *Alternaria*-treated Wt mice (FIG. 4B).

Example 4. Pla2g5-Dependent Generation of Linoleic Acid and Oleic Acid Contribute to ILC2 Activation and Pulmonary Inflammation To identify candidate Pla2g5-derived mediators generated by macrophages that could contribute to ILC2 activation, we performed an unbiased assessment of lipids constitutively released by Wt and Pla2g5-null BM-macrophages, using mass spectrometry[32]. Compared to Wt BM-macrophages, Pla2g5-null BM-macrophages produced significantly lower quantities of medium- and long-chain FFAs, mostly represented by oleic acid (OA, 18:1), LA (18:2), and AA (20:4) (FIG. 5A). Short chain FFAs were not different (data not shown).

To determine whether LA and/or OA could restore the IL-33-mediated induction of eosinophilic inflammation and ILC2 expansion, we administered intranasal LA and/or OA, alone and in combination with IL-33 (4 doses in 10 days), to Wt and Pla2g5-null mice. Neither LA nor OA alone caused pulmonary inflammation in either genotype (FIGS. 5B and C). The combination of LA+IL-33 increased the numbers of eosinophils in the lungs of Wt mice by ~3-fold when compared to IL-33 alone, and the combination of LA and OA+IL-33 further increased the numbers of eosinophils in this genotype (FIG. 5B). In contrast, LA failed to potentiate IL-33-induced eosinophilia in Pla2g5 mice, although OA+IL-33 was markedly active and the combination of LA and OA+IL-33 induced a modest further increase over IL-33+OA. The effects of FFAs on the numbers of lung ILC2 expressing IL-5 paralleled their effects on eosinophil numbers (FIG. 5C).

To determine whether LA and/or OA directly activated ILC2s, we sorted ILC2s from lungs of *Alternaria*-treated Wt and Pla2g5 null mice, rested them for 40 h, and stimulated with LA, OA, IL-33 or a combination for 8 h. Then we assayed ILC2s for their expression of intracellular IL-5. IL-33 significantly increased the percentage of IL-5-expressing ILC2s isolated from both Pla2g5-null and Wt mouse lungs. Neither LA nor OA induced significant IL-5 expression by ILC2s of either genotype. LA, but not OA, significantly potentiated IL-33-induced expression of IL-5 by Wt ILC2s, and the combination of LA+OA did not differ from the effects of LA (FIG. 6A). In contrast LA suppressed the IL-33-induced increase in IL-5 positive Pla2g5-null ILC2s (FIG. 6B). OA was inactive.

Figure 6C:
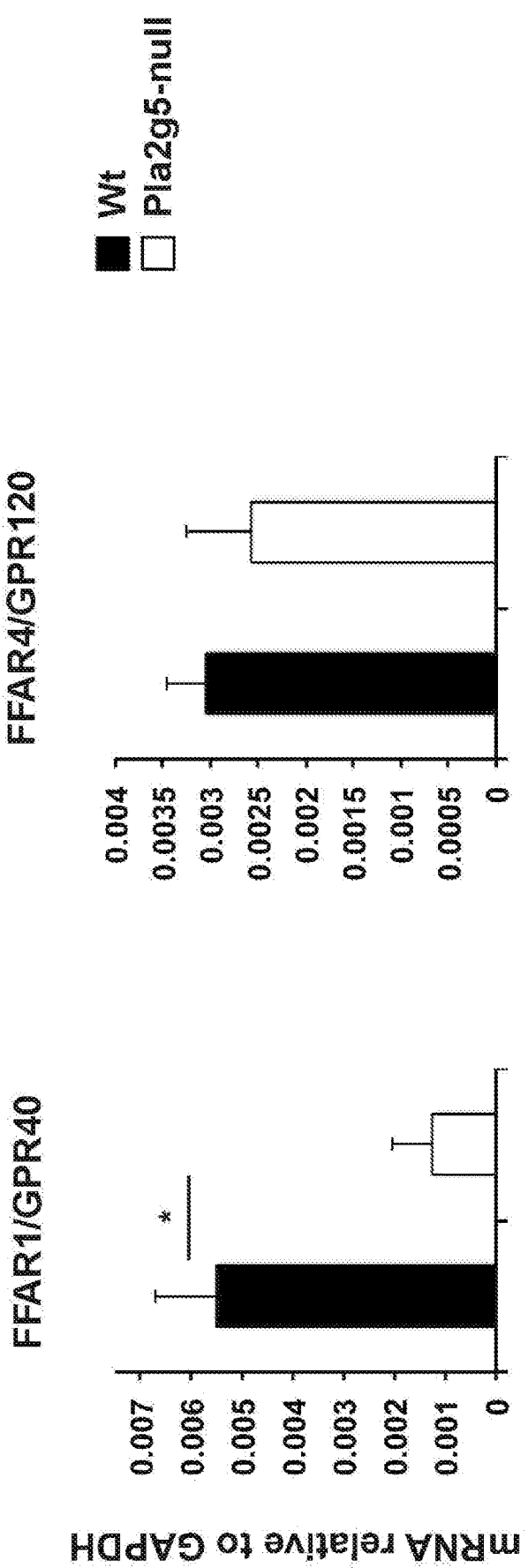

Medium-long chain FFAs signal through two G protein-coupled receptors, FFA receptor-1 (FFAR1) and FFA receptor-4 (FFAR4)[33-37]. To determine whether ILC2s expressed these receptors, and to determine the potential basis for the different responses of Wt and Pla2g5-null ILC2s to LA, we analyzed ILC2 expression of FFAR1 and FFAR4 in ILC2 sorted from Wt and Pla2g5-null *Alternaria*-treated mice. Wt ILC2s expressed FFAR1 mRNA and its expression was significantly higher compared to Pla2g5-null ILC2s (FIG. 6C). Wt and Pla2g5-null ILC2 also expressed FFAR4 mRNA to similar extents (FIG. 6C).

Example 5. Adoptive Transfer of Pla2g5-Null Macrophages into *Alternaria Alternata*-Treated Wt Mice Reduces Pulmonary Inflammation (Asthma)

Methods:

For adoptive transfer, $1\times10^5$ Wt or Pla2g5-null BM-Macs activated with a cocktail of Th2 cytokines I and generated as follows. WT and Pla2g5-null bone marrow (BM) cells were collected from femurs and tibiae of mice. The disaggregated cells were counted and suspended in complete medium containing 50 ng/ml murine r-M-CSF (PeproTech) at a concentration of $4.0\times10^5$ cells/ml, 10 ml/Petri dish. On day 3, 10 ml of medium containing r-M-CSF were added. On day 7, the cells were pulsed with 20 ng/ml of IL-4 (PeproTech), IL-33 (R&D) and GM-CSF (PeproTech) (cocktail, C) or nothing. After 24 h, cells were harvested with PBS containing Lidocaine (4 mg/ml) and EDTA (5 mM) (15 min, 37° C.) (39). For adoptive transfer, $1\times10^5$ WT and Pla2g5-null BM-macrophages (described in Ohta J I 2013), were transferred i.t. into Wt mice two days after the first dose of *Alternaria haracter* followed by 3 more doses of *Alternaria* (25 ug in 20 ul PBS) intranasally (i.n.) on day 3, 6 and 9. Mice were euthanized 18h after last dose (as in FIG. 4). Alternatively, mice received only *Alternaria haracter*, as control.

Results: This set of experiments (FIGS. 7A-B) shows that Wt mice receiving *Alternaria haracter* and BM-Macs lacking Pla2g5 have reduced numbers of eosinophils (FIG. 7A) and activated ILC2 (defined as ILC2 expressing IL5) (FIG. 7B) compared to Wt mice receiving only *Alternaria haracter* or *Alternaria haracter* plus BM-Mac with or without activation by a cocktail of Th2 cytokines.

Conclusions: These data suggest that the transfer of macrophages lacking Pla2g5 into "asthmatic" Wt mice reduces critical features of pulmonary inflammation/asthma.

REFERENCES

1. Doherty T A, Khorram N, Chang J E, Kim H K, Rosenthal P, Croft M et al. STAT6 regulates natural helper cell proliferation during lung inflammation initiated by *Alternaria*. American journal of physiology Lung cellular and molecular physiology 2012; 303(7): L577-588.
2. Kouzaki H, Iijima K, Kobayashi T, O'Grady S M, Kita H. The danger signal, extracellular ATP, is a sensor for an airborne allergen and triggers IL-33 release and innate Th2-type responses. Journal of immunology 2011; 186 (7): 4375-4387.
3. Bartemes K R, Iijima K, Kobayashi T, Kephart G M, McKenzie A N, Kita H. IL-33-responsive lineage-CD25+ CD44(hi) lymphoid cells mediate innate type 2 immunity and allergic inflammation in the lungs. Journal of immunology 2012; 188(3): 1503-1513.
4. Halim T Y, Steer C A, Matha L, Gold M J, Martinez-Gonzalez I, McNagny K M et al. Group 2 innate lymphoid cells are critical for the initiation of adaptive T helper 2 cell-mediated allergic lung inflammation. Immunity 2014; 40(3): 425-435.
5. Doherty T A, Khorram N, Sugimoto K, Sheppard D, Rosenthal P, Cho J Y et al. *Alternaria* induces STATE-dependent acute airway eosinophilia and epithelial FIZZ1 expression that promotes airway fibrosis and epithelial thickness. Journal of immunology 2012; 188(6): 2622-2629.
6. Neill D R, Wong S H, Bellosi A, Flynn R J, Daly M, Langford T K et al. Nuocytes represent a new innate effector leukocyte that mediates type-2 immunity. Nature 2010; 464(7293): 1367-1370.
7. Moro K, Yamada T, Tanabe M, Takeuchi T, Ikawa T, Kawamoto H et al. Innate production of T(H)2 cytokines by adipose tissue-associated c-Kit(+)Sca-1(+) lymphoid cells. Nature 2010; 463(7280): 540-544.
8. Price A E, Liang H E, Sullivan B M, Reinhardt R L, Eisley C J, Erle D J et al. Systemically dispersed innate IL-13-expressing cells in type 2 immunity. Proceedings of the National Academy of Sciences of the United States of America 2010; 107(25): 11489-11494.
9. Doherty T A, Khorram N, Lund S, Mehta A K, Croft M, Broide D H. Lung type 2 innate lymphoid cells express cysteinyl leukotriene receptor 1, which regulates TH2 cytokine production. The Journal of allergy and clinical immunology 2013; 132(1): 205-213.
10. Chang Y J, Kim H Y, Albacker L A, Baumgarth N, McKenzie A N, Smith D E et al. Innate lymphoid cells mediate influenza-induced airway hyper-reactivity independently of adaptive immunity. Nature immunology 2011; 12(7): 631-638.
11. Halim T Y, Krauss R H, Sun A C, Takei F. Lung natural helper cells are a critical source of Th2 cell-type cytokines in protease allergen-induced airway inflammation. Immunity 2012; 36(3): 451-463.
12. Barlow J L, Bellosi A, Hardman C S, Drynan L F, Wong S H, Cruickshank J P et al. Innate IL-13-producing nuocytes arise during allergic lung inflammation and contribute to airways hyperreactivity. The Journal of allergy and clinical immunology 2012; 129(1): 191-198 e191-194.
13. Licona-Limon P, Kim L K, Palm N W, Flavell R A. TH2, allergy and group 2 innate lymphoid cells. Nature immunology 2013; 14(6): 536-542.
14. Molofsky A B, Nussbaum J C, Liang H E, Van Dyken S J, Cheng L E, Mohapatra A et al. Innate lymphoid type 2 cells sustain visceral adipose tissue eosinophils and alternatively activated macrophages. The Journal of experimental medicine 2013; 210(3): 535-549.
15. Hardman C S, Panova V, McKenzie A N. IL-33 citrine reporter mice reveal the temporal and spatial expression of IL-33 during allergic lung inflammation. European journal of immunology 2013; 43(2): 488-498.
16. Kim H Y, Chang Y J, Subramanian S, Lee H H, Albacker L A, Matangkasombut P et al. Innate lymphoid cells responding to IL-33 mediate airway hyperreactivity independently of adaptive immunity. The Journal of allergy and clinical immunology 2012; 129(1): 216-227 e211-216.
17. Polumuri S K, Jayakar G G, Shirey K A, Roberts Z J, Perkins D J, Pitha P M et al. Transcriptional regulation of murine IL-33 by TLR and non-TLR agonists. Journal of immunology 2012; 189(1): 50-60.
18. Dennis E A, Cao J, Hsu Y H, Magrioti V, Kokotos G. Phospholipase A2 enzymes: physical structure, biological function, disease implication, chemical inhibition, and therapeutic intervention. Chemical reviews 2011; 111 (10): 6130-6185.
19. Murakami M, Taketomi Y, Miki Y, Sato H, Yamamoto K, Lambeau G. Emerging roles of secreted phospholipase A enzymes: The $3^{rd}$ edition. Biochimie 2014; 107PA: 105-113.
20. Alvarez-Curto E, Milligan G. Metabolism meets immunity: The role of free fatty acid receptors in the immune system. Biochemical pharmacology 2016; 114: 3-13.
21. Murakami M, Koduri R S, Enomoto A, Shimbara S, Seki M, Yoshihara K et al. Distinct arachidonate-releasing functions of mammalian secreted phospholipase A2s in human embryonic kidney 293 and rat mastocytoma RBL-2H3 cells through haract sulfate shuttling and external plasma membrane mechanisms. The Journal of biological chemistry 2001; 276(13): 10083-10096.
22. Sato H, Taketomi Y, Ushida A, Isogai Y, Kojima T, Hirabayashi T et al. The adipocyte-inducible secreted phospholipases PLA2G5 and PLA2G2E play distinct roles in obesity. Cell metabolism 2014; 20(1): 119-132.
23. Singer A G, Ghomashchi F, Le Calvez C, Bollinger J, Bezzine S, Rouault M et al. Interfacial kinetic and binding properties of the complete set of human and mouse groups I, II, V, X, and XII secreted phospholipases A2. The Journal of biological chemistry 2002; 277(50): 48535-48549.
24. Giannattasio G, Fujioka D, Xing W, Katz H R, Boyce J A, Balestrieri B. Group V secretory phospholipase A2 reveals its role in house dust mite-induced allergic pulmonary inflammation by regulation of dendritic cell function. Journal of immunology 2010; 185(7): 4430-4438.
25. Ohta S, Imamura M, Xing W, Boyce J A, Balestrieri B. Group V secretory phospholipase A2 is involved in macrophage activation and is sufficient for macrophage effector functions in allergic pulmonary inflammation. Journal of immunology 2013; 190(12): 5927-5938.
26. Yamaguchi M, Zacharia J, Laidlaw T M, Balestrieri B. PLA2G5 regulates transglutaminase activity of human IL-4-activated M2 macrophages through PGE2 generation. Journal of leukocyte biology 2016 July; 100(1):131-41. doi: 10.1189/jlb.3A0815-372R. Epub 2016 Mar. 2.
27. Munoz N M, Meliton A Y, Arm J P, Bonventre J V, Cho W, Leff A R. Deletion of secretory group V phospholipase A2 attenuates cell migration and airway hyperresponsiveness in immunosensitized mice. Journal of immunology 2007; 179(7): 4800-4807.
28. Wojno E D, Monticelli L A, Tran S V, Alenghat T, Osborne L C, Thome J J et al. The prostaglandin D(2) receptor CRTH2 regulates accumulation of group 2 innate lymphoid cells in the inflamed lung. Mucosal immunology 2015; 8(6): 1313-1323.
29. Stevens W W, Kim T S, Pujanauski L M, Hao X, Braciale T J. Detection and quantitation of eosinophils in the murine respiratory tract by flow cytometry. Journal of immunological methods 2007; 327(1-2): 63-74.
30. Makrinioti H, Toussaint M, Jackson D J, Walton R P, Johnston S L. Role of interleukin 33 in respiratory allergy and asthma. The Lancet Respiratory medicine 2014; 2(3): 226-237.
31. Gorski S A, Hahn Y S, Braciale T J. Group 2 innate lymphoid cell production of IL-5 is regulated by NKT cells during influenza virus infection. PloS pathogens 2013; 9(9): e1003615.
32. Quehenberger O, Armando A M, Dennis E A. High sensitivity quantitative lipidomics analysis of fatty acids in biological samples by gas chromatography-mass spectrometry. Biochimica et biophysica acta 2011; 1811(11): 648-656.
33. Briscoe C P, Tadayyon M, Andrews J L, Benson W G, Chambers J K, Eilert M M et al. The orphan G protein-coupled receptor GPR40 is activated by medium and long chain fatty acids. The Journal of biological chemistry 2003; 278(13): 11303-11311.
34. Itoh Y, Kawamata Y, Harada M, Kobayashi M, Fujii R, Fukusumi S et al. Free fatty acids regulate insulin secretion from pancreatic beta cells through GPR40. Nature 2003; 422(6928): 173-176.
35. Kotarsky K, Nilsson N E, Flodgren E, Owman C, Olde B. A human cell surface receptor activated by free fatty acids and thiazolidinedione drugs. Biochemical and biophysical research communications 2003; 301(2): 406-410.
36. Hirasawa A, Tsumaya K, Awaji T, Katsuma S, Adachi T, Yamada M et al. Free fatty acids regulate gut incretin glucagon-like peptide-1 secretion through GPR120. Nature medicine 2005; 11(1): 90-94.
37. Oh da Y, Walenta E, Akiyama 1E, Lagakos W S, Lackey D, Pessentheiner A R et al. A Gpr120-selective agonist improves insulin resistance and chronic inflammation in obese mice. Nature medicine 2014; 20(8): 942-947.
38. Barlow J L, Peel S, Fox J, Panova V, Hardman C S, Camelo A et al. IL-33 is more potent than IL-25 in provoking IL-13-producing nuocytes (type 2 innate lymphoid cells) and airway contraction. The Journal of allergy and clinical immunology 2013; 132(4): 933-941.

39. Halim T Y, MacLaren A, Romanish M T, Gold M J, McNagny K M, Takei F. Retinoic-acid-receptor-related orphan nuclear receptor alpha is required for natural helper cell development and allergic inflammation. Immunity 2012; 37(3): 463-474.
40. Wills-Karp M, Rani R, Dienger K, Lewkowich I, Fox J G, Perkins C et al. Trefoil factor 2 rapidly induces interleukin 33 to promote type 2 immunity during allergic asthma and hookworm infection. The Journal of experimental medicine 2012; 209(3): 607-622.
41. Yu S, Kim H Y, Chang Y J, DeKruyff R H, Umetsu D T. Innate lymphoid cells and asthma. The Journal of allergy and clinical immunology 2014; 133(4): 943-950; quiz 951.
42. Christiansen E, Watterson K R, Stocker C J, Sokol E, Jenkins L, Simon K et al. Activity of dietary fatty acids on FFA1 and FFA4 and haracterization of pinolenic acid as a dual FFA1/FFA4 agonist with potential effect against metabolic diseases. The British journal of nutrition 2015; 113(11): 1677-1688.
43. Heng T S, Painter M W, Immunological Genome Project C. The Immunological Genome Project: networks of gene expression in immune cells. Nature immunology 2008; 9(10): 1091-1094.
44. Van Dyken S J, Mohapatra A, Nussbaum J C, Molofsky A B, Thornton E E, Ziegler S F et al. Chitin activates parallel immune modules that direct distinct inflammatory responses via innate lymphoid type 2 and gammadelta T cells. Immunity 2014; 40(3): 414-424.
45. Lee M W, Odegaard J I, Mukundan L, Qiu Y, Molofsky A B, Nussbaum J C et al. Activated type 2 innate lymphoid cells regulate beige fat biogenesis. Cell 2015; 160(1-2): 74-87.
46. Satake Y, Diaz B L, Balestrieri B, Lam B K, Kanaoka Y, Grusby M J et al. Role of group V phospholipase A2 in zymosan-induced eicosanoid generation and vascular permeability revealed by targeted gene disruption. The Journal of biological chemistry 2004; 279(16): 16488-16494.
47. Balestrieri B, Hsu V W, Gilbert H, Leslie C C, Han W K, Bonventre J V et al. Group V secretory phospholipase A2 translocates to the phagosome after zymosan stimulation of mouse peritoneal macrophages and regulates phagocytosis. The Journal of biological chemistry 2006; 281(10): 6691-6698.
48. Quehenberger O, Armando A M, Brown A H, Milne S B, Myers D S, Merrill A H et al. Lipidomics reveals a remarkable diversity of lipids in human plasma. Journal of lipid research 2010; 51(11): 3299-3305.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing pulmonary inflammation in a subject, the method comprising:
    identifying a subject as having an allergen-induced asthma; and
    delivering a population of Pla2g5-deficient suppressive macrophages to the subject identified as having an allergen-induced asthma, preferably to a lung or airway of the subject.

2. The method of claim 1, wherein the population of Pla2g5-deficient suppressive macrophages is autologous to the subject.

3. The method of claim 1, wherein the population of Pla2g5-deficient suppressive macrophages comprises an inhibitory nucleic acid that reduces expression of Pla2g5.

4. The method of claim 3, wherein the inhibitory nucleic acid is an antisense oligonucleotide, or siRNA, shRNA.

5. The method of claim 4, wherein the inhibitory nucleic acid is modified.

6. The method of claim 5, wherein the inhibitory nucleic acid comprises a modified backbone or at least one modified nucleotide.

7. The method of claim 6, wherein the inhibitory nucleic acid comprises at least one locked nucleic acid.

8. The method of claim 5, wherein the inhibitory nucleic acid is a gapmer or mixmer.

9. The method claim 1, wherein the subject has asthma.

10. The method of claim 1, wherein the cells are delivered by an aerosol spray of a suspension of cells into a nasal passage of the subject; by intratracheal or intrabracheal distillation; or by intravenous administration.

11. A method of preparing a population of Pla2g5-deficient suppressive macrophages, the method comprising:
    obtaining a sample comprising peripheral blood from a subject;

enriching the sample for mononuclear cells;
maintaining the mononuclear cells under conditions to promote differentiation of the mononuclear cells into a population of macrophages, wherein the cells are maintained in the presence of Granulocyte macrophage colony-stimulating factor (GM-CSF), preferably for 13 days;
contacting the population of macrophages with an inhibitory nucleic acid that reduces expression of Pla2g5; and
polarizing the cells with interleukin 4 (IL-4),
thereby preparing a population of Pla2g5-deficient suppressive macrophages.

12. The method of claim 11, wherein the sample of peripheral blood is obtained from a subject who has pulmonary inflammation.

13. The method of claim 11, wherein the inhibitory nucleic acid is an antisense oligonucleotide, or siRNA, shRNA.

14. The method of claim 13, wherein the inhibitory nucleic acid is modified.

15. The method of claim 14, wherein the inhibitory nucleic acid comprises a modified backbone or at least one modified nucleotide.

16. The method of claim 14, wherein the inhibitory nucleic acid comprises at least one locked nucleic acid.

17. The method of claim 11, wherein the inhibitory nucleic acid is a gapmer or mixmer.

18. The method of claim 11, wherein the subject has asthma.

19. A population of Pla2g5-deficient suppressive macrophages prepared by the method of claim 11.

20. A method of reducing allergen-induced pulmonary inflammation in a subject, the method comprising administering the population of Pla2g5-deficient suppressive macrophages of claim 19 to a subject in need thereof.

* * * * *

UNITED STATES PATENT AND TRADEMARK OFFICE
CERTIFICATE OF CORRECTION

| | |
|---|---|
| PATENT NO. | : 11,273,176 B2 |
| APPLICATION NO. | : 16/080905 |
| DATED | : March 15, 2022 |
| INVENTOR(S) | : Barbara Balestrieri |

It is certified that error appears in the above-identified patent and that said Letters Patent is hereby corrected as shown below:

In the Claims

In Column 54, Line 59, Claim 9, after "method" insert -- of --

In Column 54, Lines 62-63, Claim 10, delete "intrabracheal distillation" and insert -- intratracheal instillation --

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: sequencing primer GAPDH F

<400> SEQUENCE: 1
tcaacagcaa ctcccactct tcca                                          24

<210> SEQ ID NO 2
<211> LENGTH: 24
<212> TYPE: DNA
<213> ORGANISM: Artificial Sequence
<220> FEATURE:
<223> OTHER INFORMATION: sequencing primer GAPDH R

<400> SEQUENCE: 2
accctgttgc tgtagccgta ttca                                          24

<210> SEQ ID NO 3
<211> LENGTH: 21
<212> TYPE: DNA
<213> ORGANISM: Artificial Sequence
<220> FEATURE:
<223> OTHER INFORMATION: sequencing primer Pla2g5 F

<400> SEQUENCE: 3
tggttcctgg cttgcagtgt g                                             21

<210> SEQ ID NO 4
<211> LENGTH: 21
<212> TYPE: DNA
```

```
<213> ORGANISM: Artificial Sequence
<220> FEATURE:
<223> OTHER INFORMATION: sequencing primer Pla2g5 R

<400> SEQUENCE: 4
ttcgcagatg actaggccat t                                              21

<210> SEQ ID NO 5
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 5
agagaaaccu acggagcua                                                 19

<210> SEQ ID NO 6
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 6
agaacgcccu gacaaacua                                                 19

<210> SEQ ID NO 7
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 7
gagaagggcu gcaacauuc                                                 19

<210> SEQ ID NO 8
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 8
gcacacaguc cuacaaaua                                                 19

<210> SEQ ID NO 9
<211> LENGTH: 1368
<212> TYPE: PRT
<213> ORGANISM: Streptococcus pyogenes

<400> SEQUENCE: 9
```

| Met | Asp | Lys | Lys | Tyr | Ser | Ile | Gly | Leu | Asp | Ile | Gly | Thr | Asn | Ser | Val |
|---|---|---|---|---|---|---|---|---|---|---|---|---|---|---|---|
| 1 |  |  |  | 5 |  |  |  |  | 10 |  |  |  |  | 15 |  |

| Gly | Trp | Ala | Val | Ile | Thr | Asp | Glu | Tyr | Lys | Val | Pro | Ser | Lys | Lys | Phe |
|---|---|---|---|---|---|---|---|---|---|---|---|---|---|---|---|
|  |  |  | 20 |  |  |  |  | 25 |  |  |  |  | 30 |  |  |

| Lys | Val | Leu | Gly | Asn | Thr | Asp | Arg | His | Ser | Ile | Lys | Lys | Asn | Leu | Ile |
|---|---|---|---|---|---|---|---|---|---|---|---|---|---|---|---|
|  |  | 35 |  |  |  |  | 40 |  |  |  |  | 45 |  |  |  |

| Gly | Ala | Leu | Leu | Phe | Asp | Ser | Gly | Glu | Thr | Ala | Glu | Ala | Thr | Arg | Leu |
|---|---|---|---|---|---|---|---|---|---|---|---|---|---|---|---|
|  | 50 |  |  |  |  | 55 |  |  |  |  | 60 |  |  |  |  |

| Lys | Arg | Thr | Ala | Arg | Arg | Arg | Tyr | Thr | Arg | Arg | Lys | Asn | Arg | Ile | Cys |
|---|---|---|---|---|---|---|---|---|---|---|---|---|---|---|---|
| 65 |  |  |  |  | 70 |  |  |  |  | 75 |  |  |  |  | 80 |

-continued

```
Tyr Leu Gln Glu Ile Phe Ser Asn Glu Met Ala Lys Val Asp Asp Ser
             85                  90                  95

Phe Phe His Arg Leu Glu Glu Ser Phe Leu Val Glu Glu Asp Lys Lys
        100                 105                 110

His Glu Arg His Pro Ile Phe Gly Asn Ile Val Asp Glu Val Ala Tyr
    115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
```

-continued

```
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
            850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
```

```
Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 10
<211> LENGTH: 1053
<212> TYPE: PRT
<213> ORGANISM: Staphylococcus aureus

<400> SEQUENCE: 10

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335
```

```
Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
            450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Arg Thr Thr
                500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
            565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
            690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750
```

```
Ile Phe Ile Thr Pro His Gln Ile Lys His Ile Lys Asp Phe Lys Asp
            755             760             765

Tyr Lys Tyr Ser His Arg Val Asp Lys Lys Pro Asn Arg Glu Leu Ile
    770             775             780

Asn Asp Thr Leu Tyr Ser Thr Arg Lys Asp Asp Lys Gly Asn Thr Leu
785             790             795                         800

Ile Val Asn Asn Leu Asn Gly Leu Tyr Asp Lys Asp Asn Asp Lys Leu
                805             810              815

Lys Lys Leu Ile Asn Lys Ser Pro Glu Lys Leu Leu Met Tyr His His
            820             825             830

Asp Pro Gln Thr Tyr Gln Lys Leu Lys Leu Ile Met Glu Gln Tyr Gly
        835             840             845

Asp Glu Lys Asn Pro Leu Tyr Lys Tyr Tyr Glu Glu Thr Gly Asn Tyr
850             855             860

Leu Thr Lys Tyr Ser Lys Lys Asp Asn Gly Pro Val Ile Lys Lys Ile
865             870             875                         880

Lys Tyr Tyr Gly Asn Lys Leu Asn Ala His Leu Asp Ile Thr Asp Asp
                885             890             895

Tyr Pro Asn Ser Arg Asn Lys Val Val Lys Leu Ser Leu Lys Pro Tyr
            900             905             910

Arg Phe Asp Val Tyr Leu Asp Asn Gly Val Tyr Lys Phe Val Thr Val
        915             920             925

Lys Asn Leu Asp Val Ile Lys Lys Glu Asn Tyr Tyr Glu Val Asn Ser
        930             935             940

Lys Cys Tyr Glu Glu Ala Lys Lys Leu Lys Lys Ile Ser Asn Gln Ala
945             950             955                         960

Glu Phe Ile Ala Ser Phe Tyr Asn Asn Asp Leu Ile Lys Ile Asn Gly
            965             970             975

Glu Leu Tyr Arg Val Ile Gly Val Asn Asn Asp Leu Leu Asn Arg Ile
            980             985             990

Glu Val Asn Met Ile Asp Ile Thr  Tyr Arg Glu Tyr Leu  Glu Asn Met
            995             1000            1005

Asn Asp  Lys Arg Pro Pro Arg  Ile Ile Lys Thr Ile  Ala Ser Lys
     1010            1015            1020

Thr Gln  Ser Ile Lys Lys Tyr  Ser Thr Asp Ile Leu  Gly Asn Leu
    1025            1030            1035

Tyr Glu  Val Lys Ser Lys Lys  His Pro Gln Ile Ile  Lys Lys Gly
    1040            1045            1050
```